United States Patent
Kawagishi et al.

(10) Patent No.: US 9,436,915 B2
(45) Date of Patent: Sep. 6, 2016

(54) MEDICAL DECISION MAKING SUPPORT APPARATUS AND CONTROL METHOD FOR THE SAME

(71) Applicant: CANON KABUSHIKI KAISHA, Tokyo (JP)

(72) Inventors: Masami Kawagishi, Yokohama (JP); Yoshio Iizuka, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 14/495,242

(22) Filed: Sep. 24, 2014

(65) Prior Publication Data

US 2015/0012474 A1 Jan. 8, 2015

Related U.S. Application Data

(63) Continuation of application No. 12/822,999, filed on Jun. 24, 2010, now Pat. No. 8,880,455, which is a continuation of application No. PCT/JP2010/000601, filed on Feb. 2, 2010.

(30) Foreign Application Priority Data

Feb. 27, 2009 (JP) ................................. 2009-047021

(51) Int. Cl.
*G06F 9/44* (2006.01)
*G06N 7/02* (2006.01)
(Continued)

(52) U.S. Cl.
CPC ............. *G06N 5/048* (2013.01); *G06F 19/321* (2013.01); *G06F 19/345* (2013.01)

(58) Field of Classification Search
None
See application file for complete search history.

(56) References Cited

U.S. PATENT DOCUMENTS

| 4,649,515 A * | 3/1987 | Thompson | G06N 5/04 706/48 |
| 5,130,936 A * | 7/1992 | Sheppard | G06F 11/2257 706/10 |

(Continued)

FOREIGN PATENT DOCUMENTS

| JP | 6-347563 | 12/1994 |
| JP | 2001-229294 A | 8/2001 |

(Continued)

OTHER PUBLICATIONS

"Differential Diagnosis Generation From a Causal Network With Probabilities" William J. Long, Shapur Naimi, M. G. Criscitiello, Greg Larsen; M.I.T. Laboratory for Computer Science, Cambridge and Tufts-New England Medical Center, Boston, Massachusetts; 1989 IEEE.*

(Continued)

*Primary Examiner* — Luis Sitiriche
(74) *Attorney, Agent, or Firm* — Carter, DeLuca, Farrell & Schmidt, LLP

(57) ABSTRACT

A medical decision making support apparatus performs the inference processing of obtaining an inference result by performing inference processing associated with medical diagnosis based on a plurality of pieces of input medical information, and the calculation processing of calculating the degree of denial or affirmation of the inference result in association with each of a plurality of partial sets including each medical information extracted from the plurality of pieces of medical information as an element. The medical decision making support apparatus presents a user an inference result obtained by the inference processing and negative information indicating medical information included in a partial set, of the plurality of partial sets, for which the degree of denial is calculated by the calculation processing.

33 Claims, 16 Drawing Sheets

(51) Int. Cl.
*G06N 7/06* (2006.01)
*G06N 5/04* (2006.01)
*G06F 19/00* (2011.01)

(56) References Cited

U.S. PATENT DOCUMENTS

| | | | | |
|---|---|---|---|---|
| 5,396,580 | A | * | 3/1995 | Fu ................ G06N 3/0427 706/12 |
| 5,935,060 | A | * | 8/1999 | Iliff ................ G06F 19/345 600/301 |
| 6,601,055 | B1 | | 7/2003 | Roberts |
| 2004/0260666 | A1 | | 12/2004 | Pestotnik et al. |
| 2006/0122467 | A1 | * | 6/2006 | Harrington ........... G06K 9/00 600/300 |
| 2007/0005523 | A1 | * | 1/2007 | Maren ............... G06N 99/005 706/14 |
| 2007/0172103 | A1 | | 7/2007 | Kadomura et al. |

FOREIGN PATENT DOCUMENTS

| | | |
|---|---|---|
| JP | 2004-288047 A | 10/2004 |
| JP | 2006-500124 A | 1/2006 |
| JP | 2006-127452 A | 5/2006 |
| JP | 2006-181037 A | 7/2006 |
| WO | 2004/029851 A1 | 4/2004 |
| WO | 2005/104953 A1 | 11/2005 |

OTHER PUBLICATIONS

Szolovits, "Uncertainty and Decisions in Medical Informatics", Laboratory for Computer Science Massachusetts Institute of Technology, Cambridge, Massachusetts, vol. 34, 1995, pp. 1-20.

Jensen et al., "Bayesian Networks and Decision Graphs", Second Edition, 2007, pp. 32-41 and pp. 152-155.

Japanese Office Action issued in corresponding application No. 2014147218 on Aug. 14, 2015.

* cited by examiner

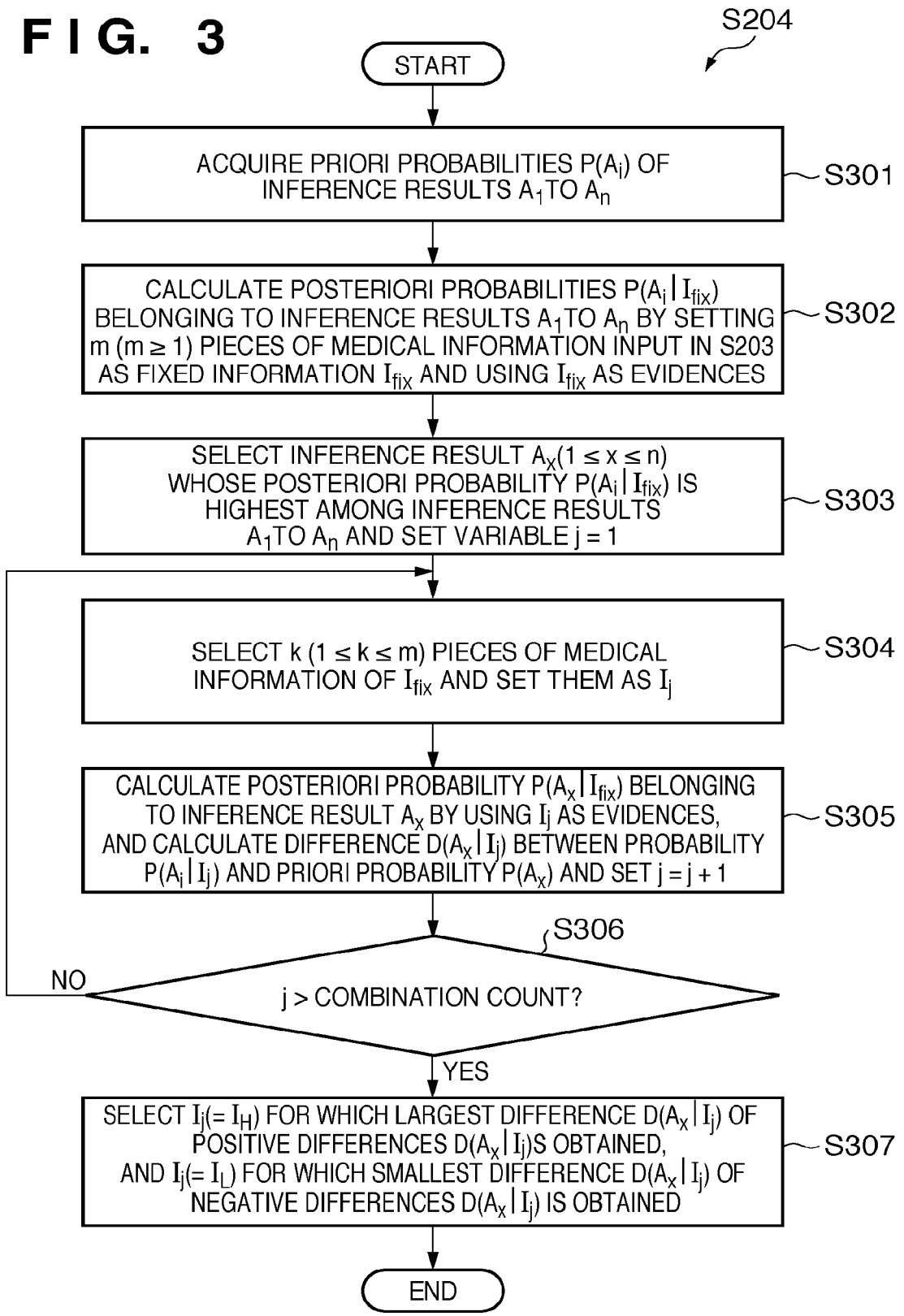

F I G. 4A

| ABNORMALITY TYPE | | SIZE OF NODUS | | |
|---|---|---|---|---|
| | | SMALL | INTERMEDIATE | LARGE |
| | PRIMARY LUNG CANCER | 10% | 40% | 50% |
| | LUNG METASTASIS | 50% | 40% | 10% |
| | OTHER ABNORMALITIES | 55% | 30% | 15% |

404

F I G. 7
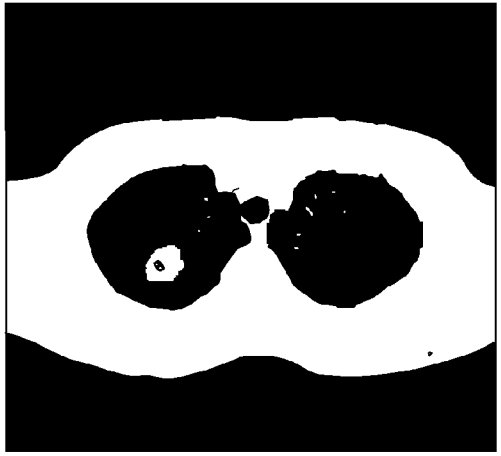

F I G. 15

INFERENCE RESULT

INTERPRETATION TARGET IMAGE

INPUT IMAGE

SIZE OF NODUS: INTERMEDIATE
SMOOTHNESS: INTERMEDIATE
VASCULAR INVOLVEMENT/
INVOLUTION: UNKNOWN
SOFT TISSUE DENSITY RATIO: HIGH
GAS DENSITY RATIO: LOW

INFERENCE RESULT ⚠ PROBABILITY DIFFERENCE HAS BECOME SMALL

LUNG METASTASIS: 49.9%

OTHER ABNORMALITIES: 40.5%

PRIMARY LUNG CANCER: 9.6%

AFFIRMATIVE INFORMATION | VASCULAR INVOLVEMENT/INVOLUTION: UNKNOWN

NEGATIVE INFORMATION | GAS DENSITY RATIO: LOW

OK

MEDICAL DECISION MAKING SUPPORT APPARATUS AND CONTROL METHOD FOR THE SAME

CROSS REFERENCE TO RELATED APPLICATIONS

This application is a Continuation of Ser. No. 12/822,999, filed Jun. 24, 2010, which is a Continuation of International Patent Application No. PCT/JP2010/000601, filed Feb. 2, 2010, which claims priority from Japanese Patent Application No. 2009-047021, filed Feb. 27, 2009. The disclosures of each of which are hereby incorporated by reference herein in their entirety.

TECHNICAL FIELD

The present invention relates to a medical decision making support apparatus that processes medical information and presents the obtained information, and a control method for the same.

BACKGROUND ART

In the medical field, doctors display medical images obtained by imaging patients on monitors, interpret the displayed medical images, and observe the states of lesions and their changes over time. Medical image data of this type are generated by, for example,
  CR (Computed Radiography) apparatus,
  CT (Computed Tomography) apparatus,
  MRI (Magnetic Resonance Imaging) apparatus,
  PET (Positron Emission Tomography) apparatus,
  SPECT image (Single Photon Emission Computed Tomography), and
  ultrasound apparatus (US: Ultrasound System).

With the aim of reducing the load of such interpretation on a doctor, an apparatus has been developed that detects, for example, an abnormal tumor shadow indicating a cancer or the like or a high-density minute calcification shadow from a medical image, and infers and presents the state of the shadow by computer processing, thereby supporting diagnosis. Such a support can reduce the load of interpretation on a doctor and improve the accuracy of an interpretation result. Such an apparatus is called a computer-aided diagnosis (CAD) apparatus.

In general, the following is a proper procedure when using such a CAD in an actual clinical case. First of all, the doctor interprets medical images first, and then refers to the diagnosis support information output from the CAD to compare it with the interpretation result obtained by himself/herself. In this operation, more specifically, the doctor associates finding information on an interpretation report, which the doctor has written by himself/herself, with finding information of the diagnosis support information calculated by the CAD to find an oversight, a detection error, a difference in finding, and the like. If, however, the CAD presents no grounds on which to infer the diagnosis support information, the doctor cannot determine whether the inference result obtained by the CAD is reliable or not. When the interpretation result obtained by the doctor differs from the result obtained by the CAD, in particular, it is important to determine the reliability of the inference result.

It is therefore necessary to provide a mechanism for presenting grounds on which the CAD system infers diagnosis support information. With regard to this, patent reference 1 discloses a technique of superimposing and displaying a marker indicating an abnormal shadow candidate and information supporting the determination of abnormality on a medical image. In addition, patent reference 2 discloses a technique of displaying features and criteria used for computer-aided detection as coded descriptors on an image. According to patent references 1 and 2 described above, it is possible to more accurately decide the types of abnormal shadow candidates by presenting the user the grounds of inference with respect to detected abnormal shadows.

PRIOR ART REFERENCE

Patent Reference

Patent Reference 1: WO2005/104953
Patent Reference 2: PCT(WO) 2006-500124

Non-Patent Reference

Non-patent Reference 1: FinnV. Jensen, Thomas D. Nielsen, "Bayesian Networks and Decision Graphs", 2007 (non-patent reference 1 is referred to in "DESCRIPTION OF EMBODIMENTS")

Although the technique described in patent reference 1 presents a reason for the detection of an abnormal shadow candidate, it presents only one reason and provides no way of handling a case in which there are many pieces of information as the grounds of inference. The technique described in patent reference 2 allows the selection of a plurality of pieces of reason information to be displayed. However, the user is in charge of selecting information to be presented, and the technique makes no determination about which information is selected and presented to the user. In addition, the techniques disclosed in patent references 1 and 2 present only affirmative information for an inference result, and hence the user can only determine the reliability of the inference result from the affirmative information alone.

SUMMARY OF THE INVENTION

According to an embodiment of the present invention, there is provided a medical decision making support apparatus which allows a user to easily and reliably determine the reliability of the inference result obtained by medical decision making support.

In order to achieve the above object, a medical decision making support apparatus according to an aspect of the present invention has the following arrangement. That is, this apparatus comprises
  inference means for obtaining an inference result by performing inference processing associated with a medical diagnosis based on a plurality of pieces of input medical information,
  calculation means for calculating a degree of one of denial and affirmation of the inference result in association with each of a plurality of partial sets including each medical information extracted from the plurality of pieces of medical information as an element, and
  presentation means for presenting an inference result obtained by the inference means and negative information indicating medical information included in a partial set, of the plurality of partial sets, for which a degree of denial is calculated by the calculation means.

According to an aspect of the present invention, a user can easily and reliably determine the reliability of the inference result obtained by medical decision making support.

Other features and advantages of the present invention will be apparent from the following description taken in conjunction with the accompanying drawings.

BRIEF DESCRIPTION OF DRAWINGS

The accompanying drawings, which are incorporated in and constitute a part of the specification, illustrate embodiments of the invention and, together with the description, serve to explain the principles of the invention.

FIG. 3 is a flowchart showing a detailed processing procedure in step S204 in FIG. 2;

FIG. 4A is a view showing a probability reasoning model using a Bayesian network;

FIG. 7 is a view showing an example of display on a monitor 104 when k=1 in the first embodiment;

FIG. 15 is a view showing an example of display on a monitor 104 in the third embodiment.

DETAILED DESCRIPTION OF EMBODIMENTS

Preferred embodiments of a medical decision making support apparatus and method according to the present invention will be described in detail below with reference to the accompanying drawings. The scope of the present invention is not limited to the embodiments shown in the accompanying drawings.

First Embodiment

Figure 1:
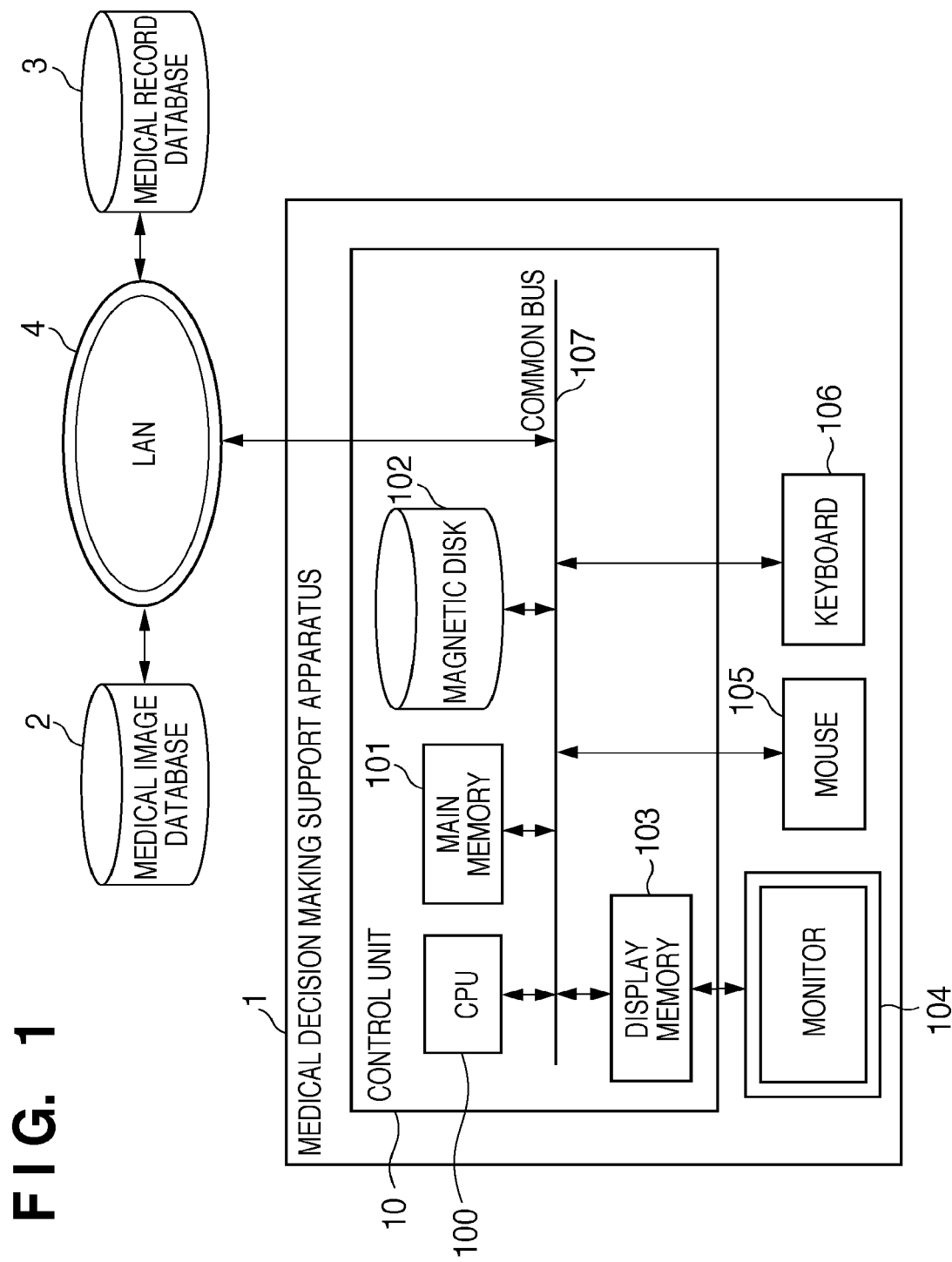
FIG. 1 is a block diagram showing an example of the configuration of a medical decision making support apparatus according to an embodiment.

FIG. 1 is a block diagram showing an example of the configuration of a medical decision making support apparatus according to the first embodiment. A medical decision making support apparatus 1 obtains an inference result by performing inference processing associated with medical diagnosis based on a plurality of pieces of input medical information, and includes a control unit 10, a monitor 104, a mouse 105, and a keyboard 106. The control unit 10 includes a central processing unit (CPU) 100, a main memory 101, a magnetic disk 102, and a display memory 103. The CPU 100 executes programs stored in the main memory 101 to perform various types of control such as communication between a medical image database 2 and a medical record database 3 and overall control of the medical decision making support apparatus 1.

The CPU 100 mainly controls the operation of each constituent element of the medical decision making support apparatus 1. The main memory 101 stores a control program to be executed by the CPU 100 and provides a work area when the CPU 100 executes a program. The magnetic disk 102 stores an operating system (OS), device drives for peripheral devices, various kinds of application software including programs for executing, for example, diagnosis support processing (to be described later), and the like. The display memory 103 temporarily stores display data for the monitor 104. The monitor 104 is, for example, a CRT monitor or a liquid crystal monitor, and displays images based on data from the display memory 103. Although an inference result is displayed on the monitor 104 designed to present a user (doctor) the inference results and the like obtained by medical decision making support in this embodiment, the embodiment may take a form of outputting inference results using a printer or the like. The mouse 105 and the keyboard 106 are operated by the user to perform pointing input operation and input characters and the like. The respective constituent elements described above are connected to each other via a common bus 107.

In this embodiment, the medical decision making support apparatus 1 reads out image data from the medical image database 2 and medical record data from the medical record database 3 via a LAN 4. In this case, it is possible to use an existing PACS (Picture Archiving and Communication System) as the medical image database 2. It is also possible to use, as the medical record database 3, an electronic medical record system which is a subsystem of an existing HIS (Hospital Information System). Alternatively, an external storage device such as an FDD, HDD, CD drive, DVD drive, MO drive, and ZIP drive may be connected to the medical decision making support apparatus 1 to allow it to read out image data and medical record data from the drives.

Note that medical images include a simple X-ray image (radiogram), X-ray CT image, MRI image, PET image, SPECT image, and ultrasonic image. In addition, medical record data to be written include the personal information of each patient (name, birth date, age, sex, and the like), clinical information (various examination values, chief complaint, past history, treatment history, and the like), reference information for the image data of each patient stored in the medical image database 2, and finding information obtained from a doctor in charge. Furthermore, a confirmed diagnosis name is written on medical record data at a progressed stage of diagnosis.

Figure 2:
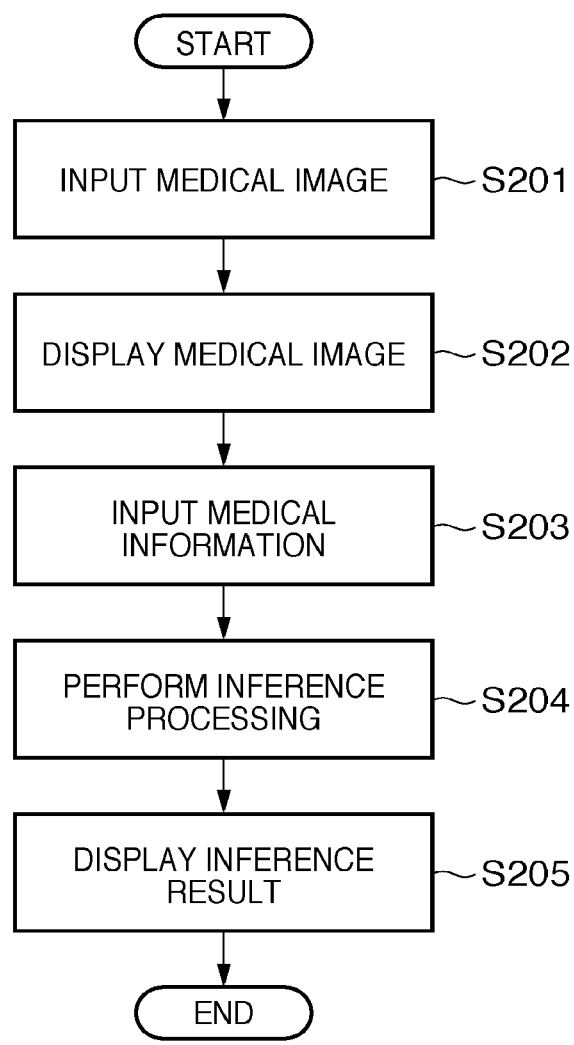
FIG. 2 is a flowchart showing a processing procedure in the first to third embodiments.

A way in which the control unit 10 controls the medical decision making support apparatus 1 will be described next with reference to the flowchart of FIG. 2. Note that the CPU 100 implements the processing shown in the flowchart of FIG. 2 by executing a program stored in the main memory 101.

In step S201, the CPU 100 inputs desired medical image data to the medical decision making support apparatus 1 in accordance with inputs via the mouse 105 and the keyboard 106. The medical image data input in step S201 will be referred to as an interpretation target image hereinafter. In this image data input processing, for example, the CPU 100 receives medical image data as an interpretation target image from the medical image database 2, which stores captured medical image data, via the LAN 4. Alternatively, the CPU 100 reads out image data as an interpretation target image from each type of storage medium such as an FDD, CD-RW drive, MO drive, or ZIP drive connected to the medical decision making support apparatus 1. In step S202, the CPU 100 displays the interpretation target image input to the medical decision making support apparatus 1 on the monitor 104.

In step S203, the doctor inputs interpretation findings to the medical decision making support apparatus 1 by using the mouse 105 and the keyboard 106 while seeing the interpretation target image displayed on the monitor 104. At this time, it is possible to use an interpretation finding input support method using a template form. Alternatively, it is possible to input the image feature amounts obtained by image processing. Each input interpretation finding/image feature amount will be referred to as medical information hereinafter. In step S204, the CPU 100 executes the processing of obtaining medical diagnosis information from the medical information of the interpretation target image input in step S203 by computer processing. That is, the CPU 100 performs inference processing for the medical information input to the medical decision making support apparatus 1. A detailed processing procedure in step S204 will be described below with reference to FIG. 3. Data indicated by I, for example, $I_{fix}$, represents a set of one or more pieces of medical information.

FIG. 3 is a flowchart showing a detailed processing procedure in step S204. In step S301, the CPU 100 acquires the probabilities (priori probabilities) of inference results $A_1$ to $A_n$ by using a probability reasoning model when no evidence (to be described later) is input, and stores the resultant information in the main memory 101. This probability reasoning model is, for example, a Bayesian network like that shown in FIGS. 4A and 4B.

A Bayesian network is a model expressing phenomena with a plurality of events and the causality relationships between the events. The relationship between events is represented by a probability. Events constituting a target phenomenon are represented by a node 401. The relationship between nodes is represented by a link 402. Each link is expressed by an arrow. A node at the root of each arrow will be referred to as a parent node. A node at the point of each arrow will be referred to as a child node. Each node has a plurality of states 403 indicating the states of the node. An occurrence probability (priori probability) is assigned to each state. The relationship between a parent node and a child node is given by a conditional probability conditioned on the parent node. A table of such conditional probabilities will be referred to as a conditional probability table 404 (CPT: Conditional Probability Table).

Information indicating in which state at least one node of a target model is will be referred to as an evidence. It is possible to obtain the probability (called posteriori probability) of a target node by a belief propagation method using this evidence, CPT, and Bayes' theorem (equation (1) (non-patent reference 1)).

[Mathematical 1]

$$P(A|B) = \frac{P(B|A)P(A)}{P(B)} \quad (1)$$

Figure 4B:
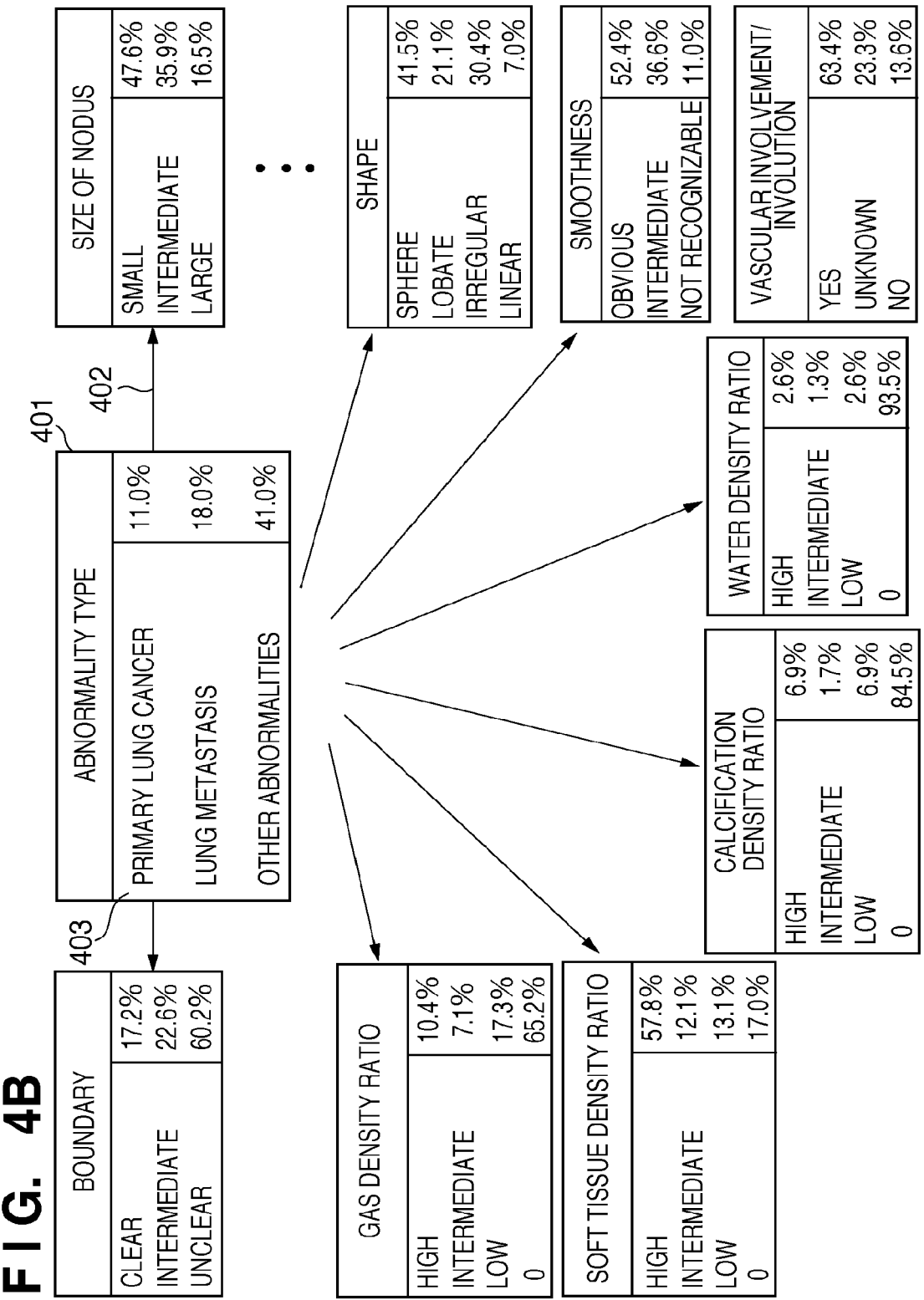
FIG. 4B is a view showing a probability reasoning model using a Bayesian network.

FIGS. 4A and 4B show a reasoning model associated with abnormal shadows in the lungs, with each node corresponding to a finding from an interpretation doctor. For example, "calcification density ratio" represents the ratio of a calcified portion in an abnormal shadow to the shadow. Likewise, "water density ratio", "soft tissue density ratio", and "gas density ratio" each are its ratio to the shadow. "Vascular involvement/involution" represents the occurrence/non-occurrence of vascular involvement/involution inside organs in the surrounding lung fields. Note that densities associated with abnormal shadows include those of substances other than those described above (for example, a metal). In some cases, such information is not input as medical information. That is, the total sum is not always 100%.

Figure 5:
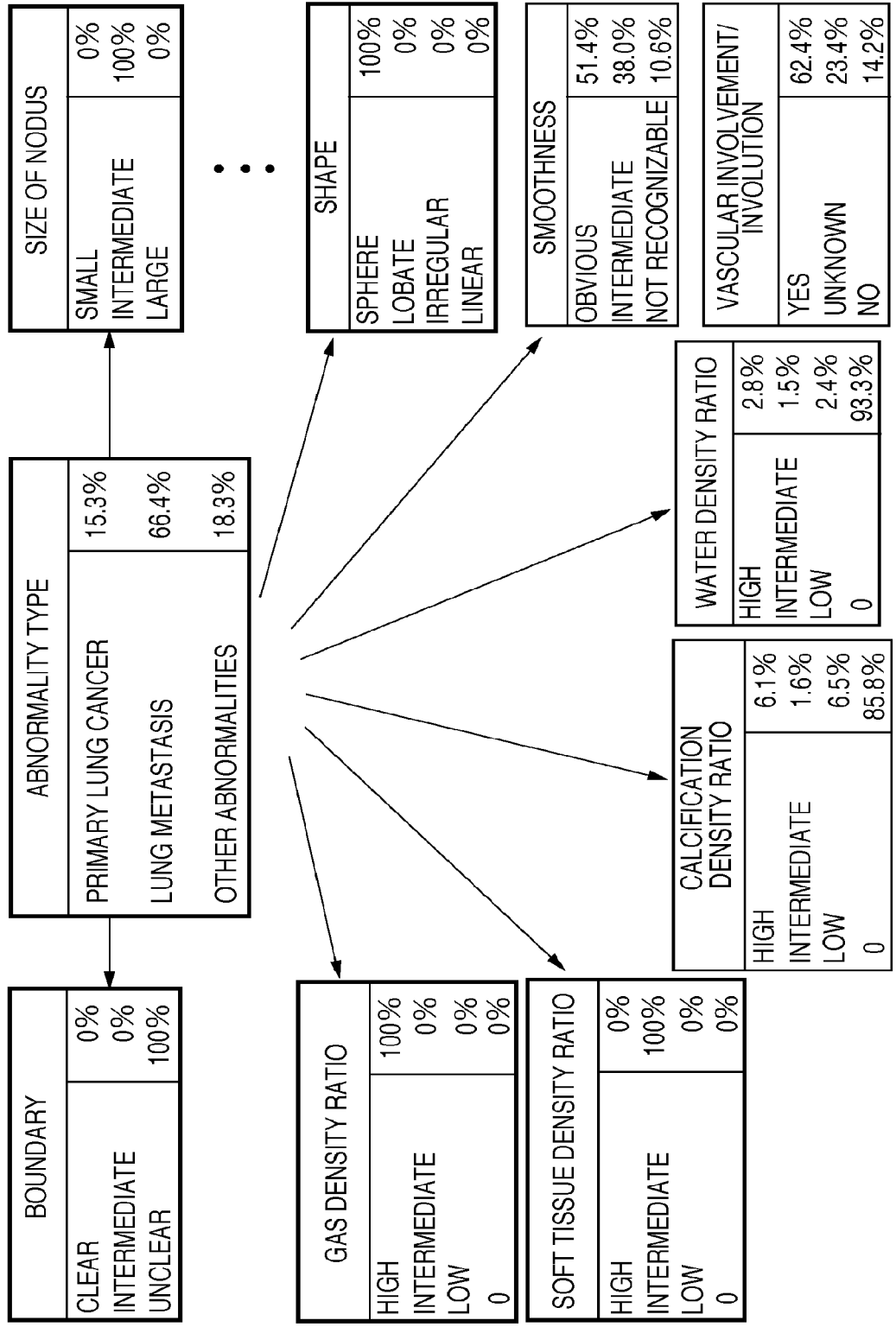
FIG. 5 is a view showing an example in which several evidences are input to the probability reasoning model in FIG. 4B.

FIG. 4B shows a state in which no evidence is input. The numerical value provided on a side of each state of each node indicates the priori probability of the state. For example, the priori probabilities of the respective states of "abnormality type" are follows: "abnormality type: primary lung cancer": 11.0%, "abnormality type: lung metastasis": 48.0%, and "abnormality type: other abnormalities": 41.0%. FIG. 5 shows a state in which evidences are input to some of the plurality of nodes in the Bayesian network shown in FIG. 4B. Each input evidence corresponds to a probability of 100% as the probability of a corresponding state as of "boundary", "shape", or the like.

In step S302, the CPU 100 sets the m (m≥1) pieces of medical information input in step S203 as fixed information (to be referred to as $I_{fix}$ hereinafter), and calculates probabilities belonging to inference results $A_1$ to $A_n$ (n≥2) by a probability reasoning model using $I_{fix}$ as evidences. That is, the fixed information $I_{fix}$ is a set of m pieces of medical information. In step S303, the CPU 100 selects an inference result $A_x$ (1≤x≤n) with the highest probability of the posteriori probabilities calculated in step S302. At the same time, the main memory 101 stores the inference results $A_1$ to $A_n$ and their probabilities. In addition, a variable j is prepared, and j=1 is set.

In step S304, the CPU 100 selects k (1≤k≤m) pieces of medical information of $I_{fix}$ and stores them as partial information $I_j$ of the fixed information in the main memory 101. That is, the partial information $I_j$ is a partial set of the fixed information $I_{fix}$ which is obtained by extracting k pieces of medical information from the fixed information $I_{fix}$. In step S305, the CPU 100 calculates a posteriori probability belonging to the inference result $A_x$ by the probability reasoning model using $I_j$ selected in step S304 as evidences. The CPU 100 calculates the difference (to be referred to as $D(A_x|I_j)$) between the calculation result and the priori probability of $A_x$ acquired in step S301, and stores the difference in association with $I_j$ stored in the main memory 101 in step S304. The CPU 100 then adds 1 to the variable j. In this manner, the CPU 100 calculates the degree of denial or affirmation with respect to the inference result obtained in step S303 for each of the plurality of partial sets $I_j$ including the pieces of medical information extracted as elements from the plurality of pieces of medical information.

In step S306, the CPU 100 compares the value of j with the total number of combinations (to be referred to as a combination count hereinafter) of $I_j$ of k pieces of medical information selected from $I_{fix}$. If j is smaller than the combination count, since the CPU 100 has not acquired the posteriori probabilities of all $I_j$, the process returns to step S304 to continue the above processing. If j is larger than the combination count, the CPU 100 executes step S307.

In step S307, the CPU 100 compares $D(A_x|I_j)$ associated with $I_j$ stored in step S304. The CPU 100 stores, in the main memory 101, $I_j$ (to be referred to as $I_H$ hereinafter) from which maximum $D(A_x|I_j)$ (with the maximum absolute value) is obtained among positive $D(A_x|I_j)$. The CPU 100 also stores, in the main memory 101, $I_j$ (to be referred to as $I_L$ hereinafter) from which minimum $D(A_x|I_j)$ (with the maximum absolute value) is obtained among negative $D(A_x|I_j)$. At this time, if there is no $I_j$ whose $D(A_x|I_j)$ is positive, a NULL value is input to $I_H$. Likewise, if there is no $I_j$ whose $D(A_x|I_j)$ is negative, a NULL value is input to $I_L$. If a NULL value is input, $I_H$ or/and $I_L$ is not displayed in step S205. $I_j$ whose $D(A_x|I_j)$ is positive indicates information which increases the probability of the inference result $A_x$. $I_j$ whose $D(A_x|I_j)$ is negative indicates information which decreases the probability of the inference result $A_x$. Therefore, $I_H$ is a reason for affirming the inference result, and $I_L$ is a reason for denying the inference result.

In step S205, the CPU 100 displays the inference processing results processed in step S204. The CPU 100 displays the inference results $A_1$ to $A_n$, their posteriori probabilities, and $I_H$ and $I_L$ stored in the main memory 101 on the monitor 104.

Cases in which k=1 and k=2 will be described below as concrete examples.

In step S301, the CPU 100 acquires 11.0%, 48.0%, and 41.0% which are respectively the priori probabilities of the inference results: "abnormality type: primary lung cancer", "abnormality type: lung metastasis", and "abnormality type: other abnormalities". In step S302, the CPU 100 calculates the posteriori probabilities of the inference results: "abnormality type: primary lung cancer", "abnormality type: lung metastasis", and "abnormality type: other abnormalities" by using $I_{fix}$ input in step S203 as evidences. The calculated posteriori probabilities of the respective inference results are 15.3%, 66.4%, and 18.3%, respectively (FIG. 5). The CPU 100 therefore stores these calculation results and selects "abnormality type: lung metastasis" with the highest posteriori probability in step S303.

Figure 6:
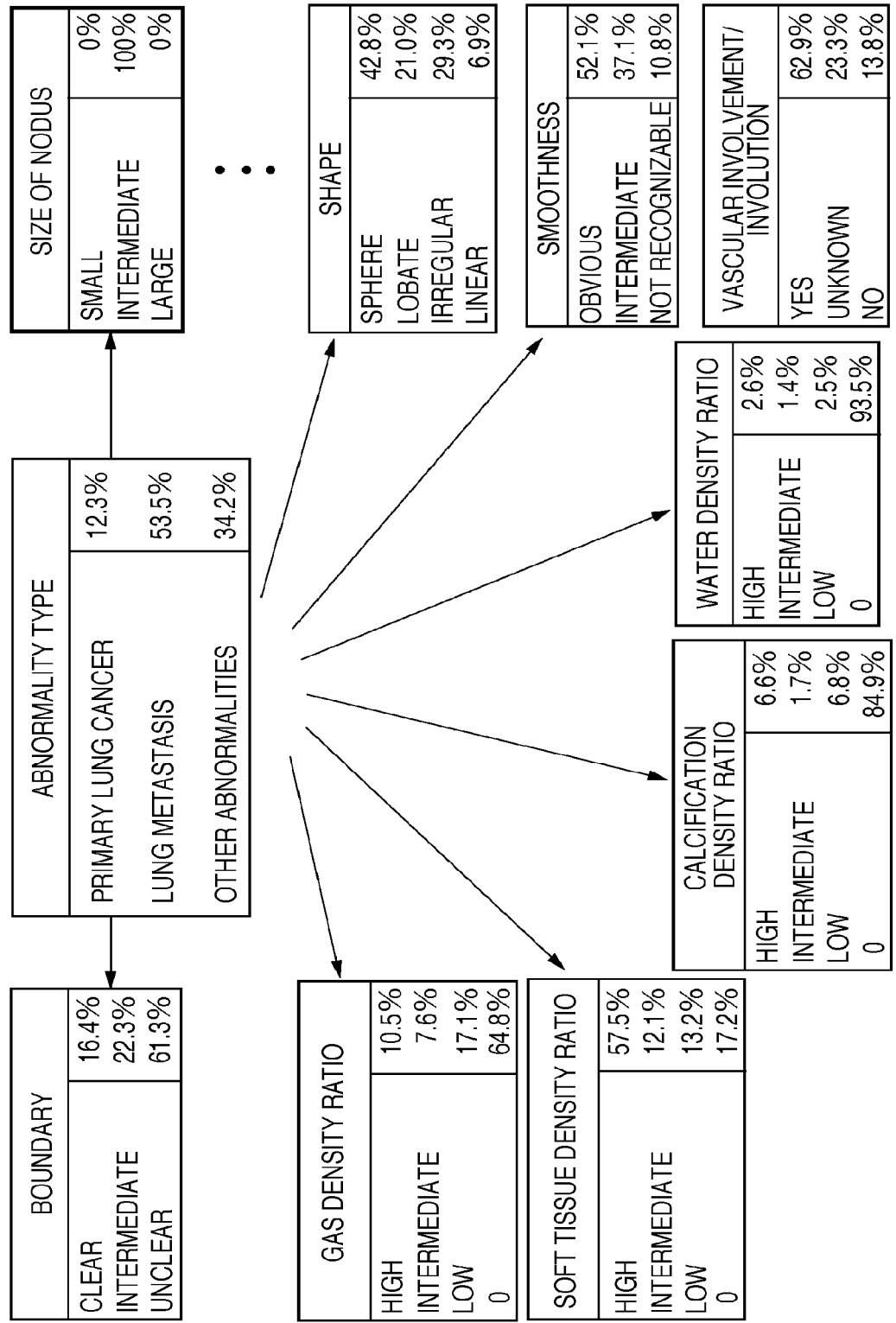
FIG. 6 is a view showing an example in which one evidence is input to the probability reasoning model in FIG. 4B.

FIG. 6 shows a case in which the medical information "size of nodus: intermediate" is selected from $I_{fix}$ by setting k=1, and is set as partial information $I_1$ of the fixed information. The CPU 100 calculates a posteriori probability belonging to the inference result "abnormality type: lung metastasis" selected in step S303 by using $I_1$ as an evidence. The CPU 100 then calculates the difference between 53.5% obtained as a calculation result and the posteriori probability, 48.0%, of "abnormality type: lung metastasis" obtained in step S301. The CPU 100 stores 5.5% obtained as a result in association with $I_1$.

Table 1 shows all $I_j$ with k=1, the posteriori probabilities of the inference result "abnormality type: lung metastasis" calculated by using $I_j$ as evidences, and the differences between the posteriori probabilities and the priori probabilities. Comparing the differences will reveal that when $I_j$ is "shape: sphere", $I_j$ takes the maximum difference, 17.9%, among the positive differences, whereas when $I_j$ is "gas density ratio: high", $I_j$ takes the maximum difference, −11.0%, among the negative differences. Therefore, $I_H$ is "shape: sphere", and $I_L$ is "gas density ratio: high".

TABLE 1

| $I_j$ (k = 1) | $P(A_x|I_j)$ | $D(A_x|I_j)$ |
| --- | --- | --- |
| Size of Nodus: Intermediate | 53.5% | 5.5% |
| Shape: Sphere | 65.9% | 17.9% |
| Soft Tissue Density Ratio: Low | 40.4% | −7.6% |
| Gas Density Ratio: High | 37.0% | −11.0% |
| Boundary: Unclear | 59.9% | 11.9% |

$P(A_x = A_2) = 48.0\%$

FIG. 7 shows an example of display on the monitor 104 when k=1. FIG. 7 shows "abnormality type: primary lung cancer", "abnormality type: lung metastasis", and "abnormality type: other abnormalities" as the inference results $A_1$ to $A_n$ and, and 15.3%, 66.4%, and 18.3% respectively calculated as the posteriori probabilities of the inference results by using $I_{fix}$ as evidences. FIG. 7 further shows $I_H$ "shape: sphere" as a reason for affirming the inference result with the highest probability, and $I_L$ "gas density ratio: high" as a reason for denying the inference result.

Figure 8:
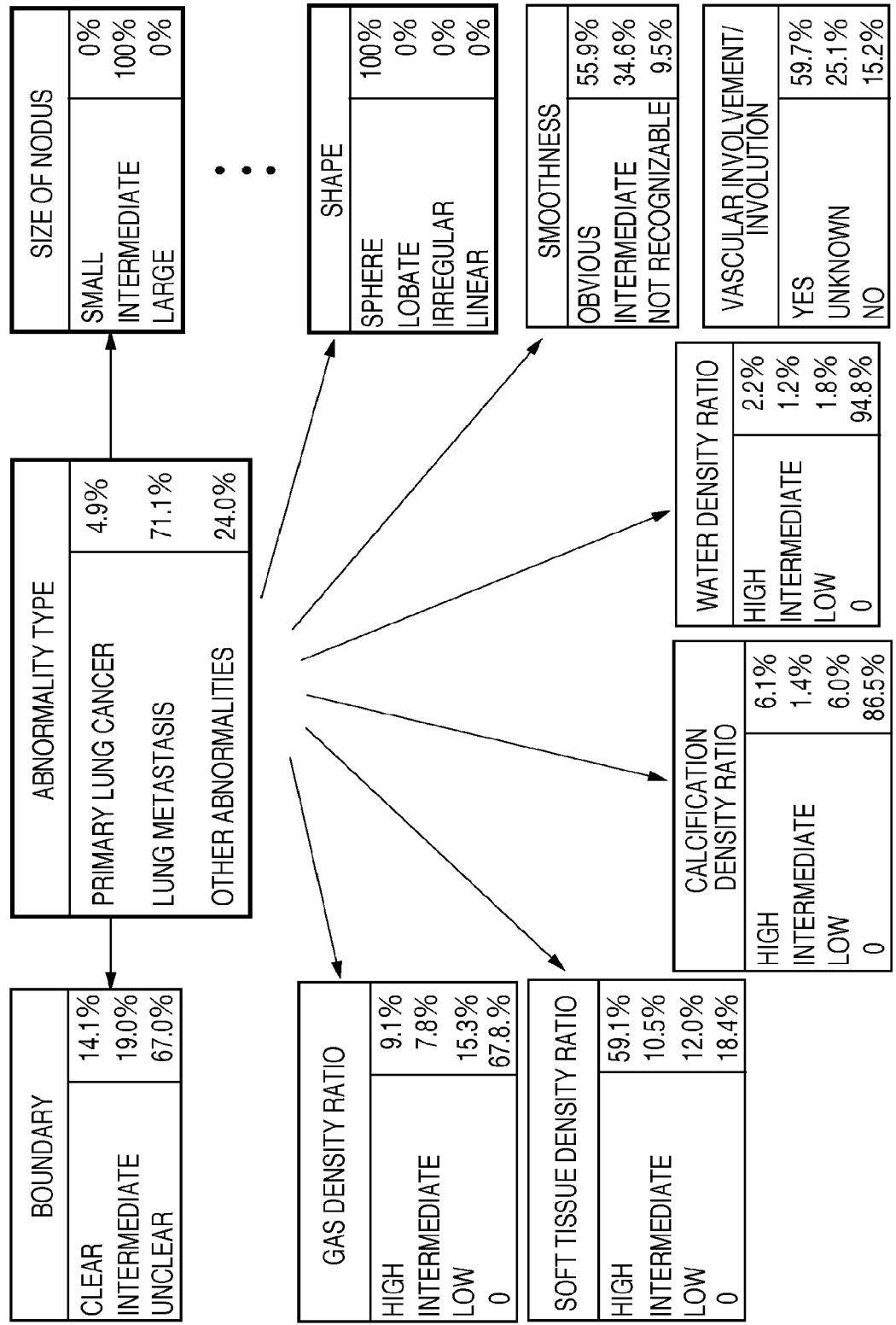
FIG. 8 is a view showing an example in which two evidences are input to the probability reasoning model in FIG. 4B.

FIG. 8 shows a case in which the pieces of medical information "size of nodus: intermediate" and "shape: sphere" are selected from $I_{fix}$ by setting k=2, and are set as partial information $I_1$ of fixed information. The CPU 100 calculates a posteriori probability belonging to the inference result "abnormality type: lung metastasis" selected in step S303 by using $I_1$ as evidences. The CPU 100 then calculates the difference between 71.1% obtained as a calculation result and the priori probability, 48.0%, of "abnormality type: lung metastasis" obtained in step S301. The CPU 100 stores 23.1% obtained as a result in association with $I_1$.

Table 2 shows all $I_j$ with k=2, the posteriori probabilities of the inference result "abnormality type: lung metastasis" calculated by using $I_j$ as evidences, and the differences between the posteriori probabilities and the priori probabilities. Comparing the differences will reveal that when $I_j$ is "shape: sphere" and "boundary: unclear", $I_j$ takes the maximum difference, 27.2%, among the positive differences, whereas when $I_j$ is "soft tissue density ratio: low" and "gas density ratio: high", $I_j$ takes the minimum difference, −21.7%, among the negative differences. Therefore, $I_H$ is "shape: sphere" and "boundary: unclear", and $I_L$ is "soft tissue density ratio: low" and "gas density ratio: high".

TABLE 2

| $I_j$ (k = 2) | | $P(A_x|I_j)$ | $D(A_x|I_j)$ |
| --- | --- | --- | --- |
| Size of Nodus: Intermediate | Shape: Sphere | 71.1% | 23.1% |
| Size of Nodus: Intermediate | Soft Tissue Density Ratio: Low | 44.6% | −3.4% |
| Size of Nodus: Intermediate | Gas Density Ratio: High | 40.6% | −7.4% |
| Size of Nodus: Intermediate | Boundary: Unclear | 65.4% | 17.4% |
| Shape: Sphere | Soft Tissue Density Ratio: Low | 60.5% | 12.5% |
| Shape: Sphere | Gas Density Ratio: High | 57.9% | 9.9% |
| Shape: Sphere | Boundary: Unclear | 75.2% | 27.2% |
| Soft Tissue Density Ratio: Low | Gas Density Ratio: High | 26.3% | −21.7% |
| Soft Tissue Density Ratio: Low | Boundary: Unclear | 53.8% | 5.8% |
| Gas Density Ratio: High | Boundary: Unclear | 50.8% | 2.8% |

$P(A_x = A_2) = 48.0\%$

Figure 9:
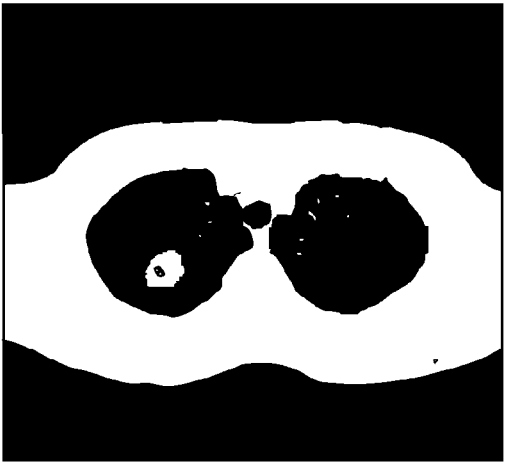
FIG. 9 is a view showing an example of display on the monitor 104 when k=2 in the first embodiment.

FIG. 9 shows an example of display on the monitor 104 when k=2. FIG. 9 shows "abnormality type: primary lung cancer", "abnormality type: lung metastasis", and "abnormality type: other abnormalities" as the inference results $A_1$ to $A_n$, and 15.3%, 66.4%, and 18.3% respectively calculated as the posteriori probabilities of the inference results by using $I_{fix}$ as evidences. FIG. 9 further shows $I_H$ "shape: sphere" and "boundary: unclear" as reasons for affirming the inference result with the highest posteriori probability, and $I_L$ "soft tissue density ratio: low" and "gas density ratio: high" as reasons for denying the inference result.

In either of the cases of k=1 and k=2, it is preferable to display the inference results $A_1$ to $A_n$ in descending order of posteriori probability calculated by using $I_{fix}$ as evidences. However, the present invention is not limited to this.

Displaying both reasons for affirming an inference result and reasons for denying the inference result can make the user feel, for example, the necessity to determine the reliability of the presented inference result, verify the reliability of input medical information, and consider a diagnosis other than the presented inference result.

According to the arrangement described above, the following effects can be obtained:

(1) Performing inference using part of medical information after inference using the medical information of an abnormal shadow makes it possible to determine medical information contributing to an inference result with the highest probability and narrow down and present information as grounds for inference.

(2) Presenting inference reasons for denying an inference result can make the user feel, for example, the necessity to verify the reliability of input medical information and consider a diagnosis other than the presented inference result with the highest probability.

Modification of First Embodiment

Step S201 is not limited to the input of medical image data. It is possible to input medical examination data including an interpretation report and information necessary for diagnosis support processing. In this case, the apparatus may have an arrangement for allowing the user to directly input these data or an arrangement capable of reading data from various types of storage media such as an FDD, CD-RW drive, MO drive, and ZIP drive on which information is recorded. It is also possible to provide an arrangement for allowing the medical decision making support apparatus 1 to receive these data from a database, on which the data are recorded, by connecting the medical decision making support apparatus 1 to the database via a LAN.

In addition, the generation of diagnosis information by inference processing in step S204 may take the following form. That is, a processing target is not limited to medical image data. For example, a processing target can include medical examination data including a past interpretation report or medical record concerning an object or other types of information which can be used for diagnosis support processing. In this case, it is possible to generate diagnosis information based on medical examination data other than image information of an object.

In addition, when partial information $I_j$ of fixed information is to be selected in step S304, k pieces of information of $I_{fix}$ or less may be selected. For example, in each of the cases of k=1 and k=2, the partial information $I_j$ may be acquired, and $I_H$ and $I_L$ described above may be acquired by using these pieces of information.

Furthermore, it is possible to select a plurality of reasons for affirming an inference result or reasons for denying the inference result in step S307. In this case, the user may determine the number of reasons to be selected, or all reasons exceeding a given threshold may be selected. In this case, the user may determine a threshold. If there is a reason for denial, a warning may be displayed. An example of determining the execution/non-execution of display by using a threshold will be described in the second embodiment.

In step S205, all the inference results $A_1$ to $A_n$ are displayed. However, only an inference result with the highest posteriori probability may be displayed. Alternatively, only some inference results may be displayed. In this case, the user may determine the number of inference results to be selected. In addition, inference results with posteriori probabilities exceeding a threshold, for example, posteriori probabilities equal to or more than 30%, may be displayed. However, the threshold to be set is not limited to the above example, and the user may determine a threshold.

Second Embodiment

The second embodiment will be described next. Note that the arrangement of the second embodiment is the same as that of the first embodiment. For this reason, the block diagram of FIG. 1 will be used, and a description of the arrangement will be omitted. Control performed by a control unit 10 in the second embodiment is almost the same as that in the first embodiment (FIG. 2). However, this control differs from that in the first embodiment in the inference processing in step S204 and the inference result display processing in step S205. These processes will be described below with reference to the flowcharts of FIGS. 10 and 11.

Figure 10:
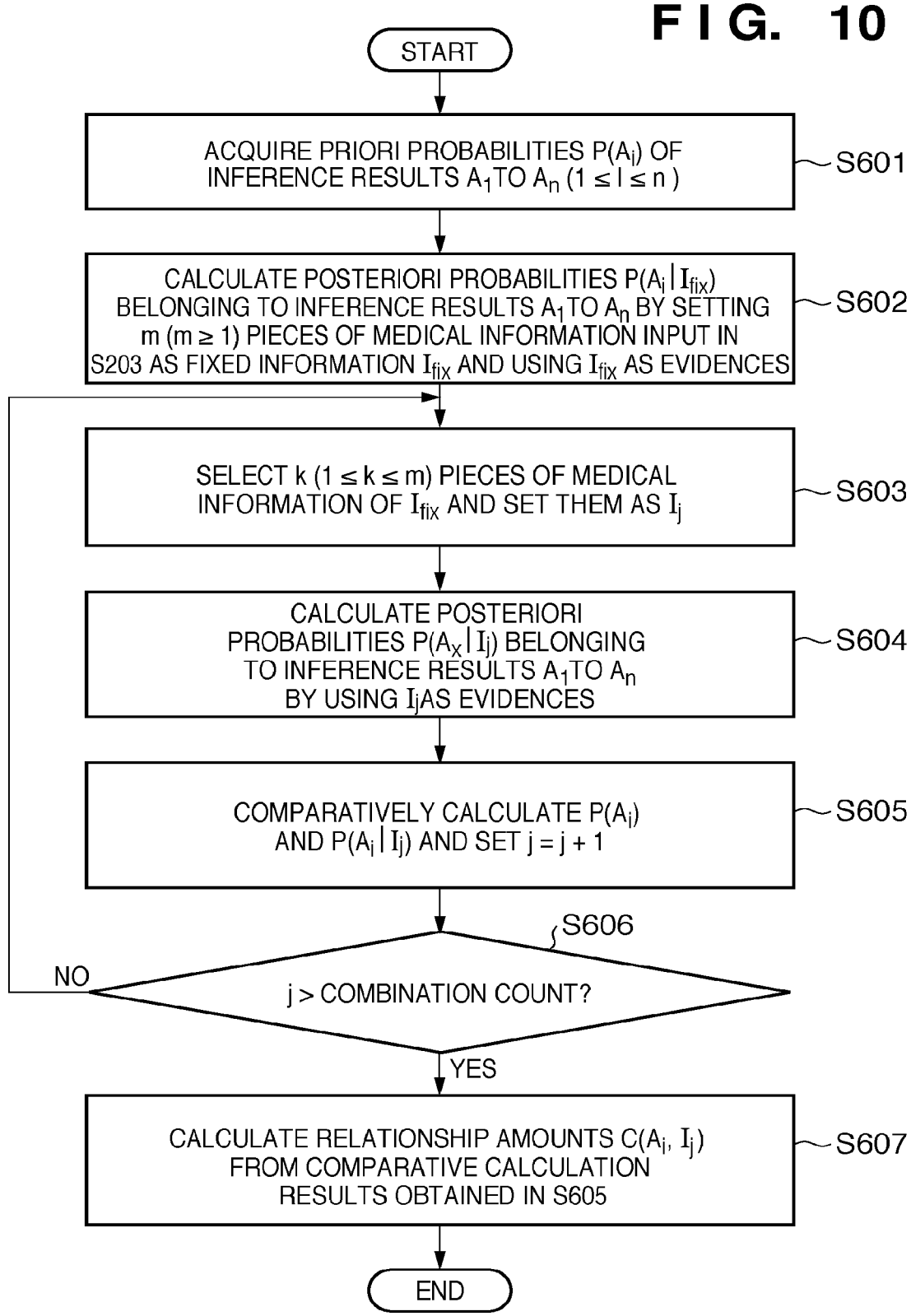
FIG. 10 is a flowchart showing a detailed processing procedure in step S204 in FIG. 2.

FIG. 10 is a flowchart showing a detailed processing procedure in step S204 in the second embodiment. In step S601, a CPU 100 acquires probabilities (priori probabilities) of inference results $A_1$ to $A_n$ without any evidence input by using a probability reasoning model, and stores them in a main memory 101. In step S602, the CPU 100 calculates probabilities belonging to the predetermined inference results $A_1$ to $A_n$ (n≥2) by using the probability reasoning model using m (m≥1) pieces of medical information input in step S503 as fixed information (to be referred to as $I_{fix}$ hereinafter). The CPU 100 also prepares a variable j and sets j=1.

In step S603, the CPU 100 selects k (1≤k≤m) pieces of medical information of $I_{fix}$, and stores them as partial information $I_j$ of the fixed information in the main memory 101. In step S604, the CPU 100 calculates posteriori probabilities belonging to the inference results $A_1$ to $A_n$ by the probability reasoning model using the tentative information $I_j$ selected in step S603 as evidences. The CPU 100 stores the calculation results in the main memory 101 in associated with stored $I_j$ in step S603. In step S605, the CPU 100 comparatively calculates the priori probabilities of the inference results $A_1$ to $A_n$ obtained in step S601 and the posteriori probabilities of the inference results $A_1$ to $A_n$ by using $I_j$ obtained in step S604 as evidences, and stores the calculation results in association with $I_j$. The CPU 100 then adds 1 to the variable j. As a comparative calculation method, for example, a method of calculating the differences between posteriori probabilities and priori probabilities is available.

In step S606, the CPU 100 compares the value of j with the total number of combinations (to be referred to as a combination count hereinafter) of $I_j$ of k pieces of medical information selected from $I_{fix}$. If j is smaller than the combination count, since the CPU 100 has not acquired the posteriori probabilities of all $I_j$, the process returns to step S603 to continue the above processing. If j is larger than the combination count, the CPU 100 executes step S607. In step S607, the CPU 100 calculates values (to be referred to as relationship amounts $C(A_i, I_j)$ hereinafter) indicating the relationships between the calculation results associated with $I_j$ obtained in step S605 and the inference results, and stores the calculation results in association with $I_j$. For example, relationship amounts are calculated by a method of determining a relationship amount from the difference between a calculated posteriori probability and a priori probability and table 4 described later for each partial set, or a method of calculating the absolute values of the differences between calculated posteriori probabilities and priori probabilities for the respective partial sets, and normalizing the values with reference to the maximum value among them.

This relationship amount calculation corresponds to the calculation of a degree associated with an inference result.

With the above operation, the processing in step S204 is terminated. In step S205, the CPU 100 displays the inference processing results processed in step S204. A detailed processing procedure in step S205 will be described below with reference to FIG. 11.

Figure 11:
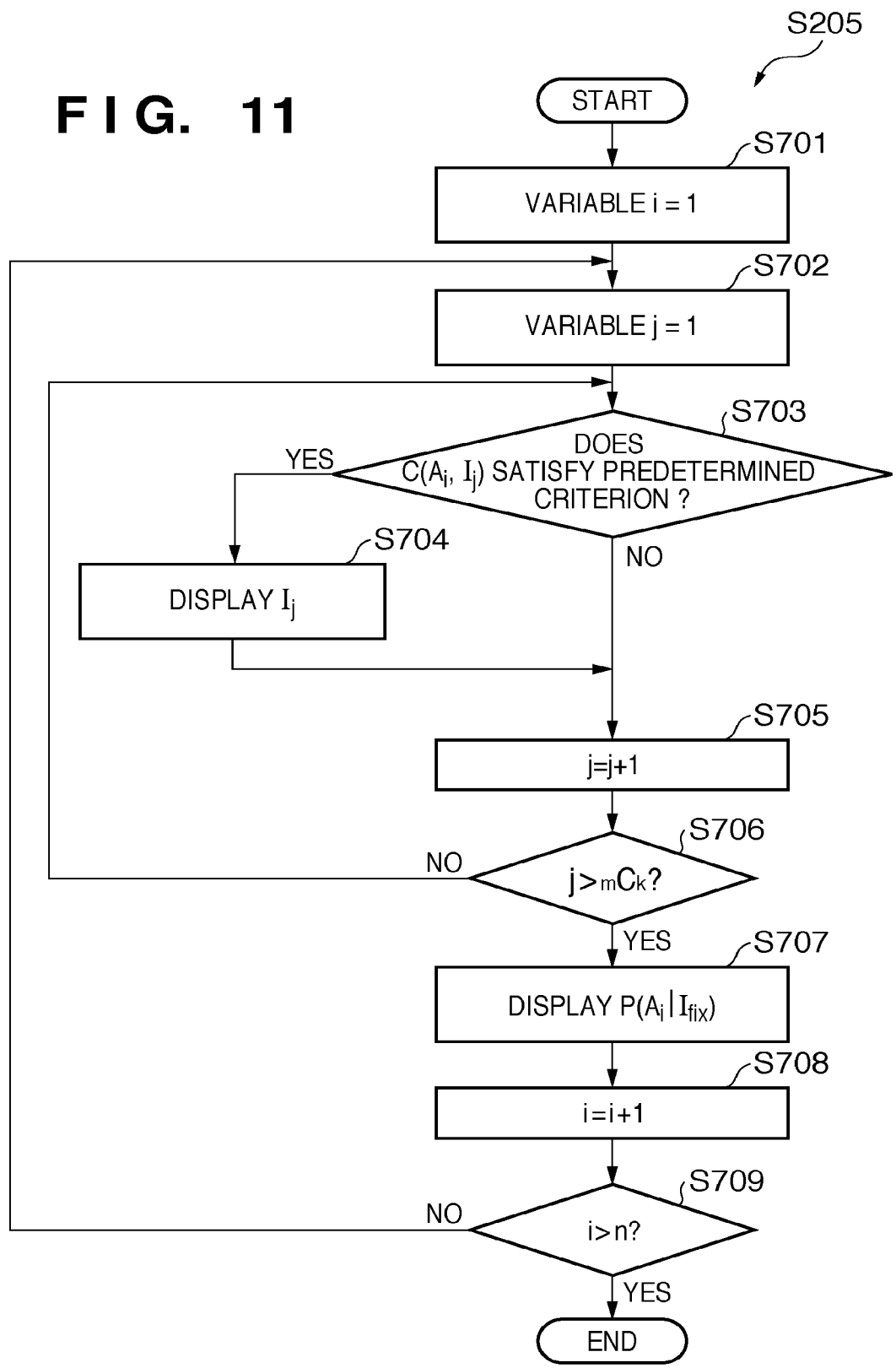
FIG. 11 is a flowchart showing a detailed processing procedure in step S205 in FIG. 2.

FIG. 11 is a flowchart showing the detailed processing procedure (for inference result display) in step S205. In step S701, the CPU 100 prepares a variable i in the main memory 101 and sets i=1. In step S702, the CPU 100 prepares a variable j in the main memory 101 and sets j=1. In step S703, the CPU 100 determines whether a relationship amount stored in the main memory 101 satisfies a predetermined criterion. If the relationship amount satisfies the predetermined criterion, the CPU 100 performs the processing in step S704. The process then advances to step S705. If the relationship amount does not satisfy the criterion, the CPU 100 skips the processing in step S704. In step S704, the CPU 100 displays $I_j$ stored in the main memory 101 on a monitor 104. At this time, the CPU 100 simultaneously displays whether $I_j$ is a reason for affirming the inference result $A_i$ or a reason for denying it, in accordance with the relationship amount. A reason for affirming the inference result $A_i$ is information that increases the probability of the inference result $A_i$. A reason for denying the inference result is information that decreases the probability. If, for example, relationship amounts are defined as indicated by table 4 (to be described later), a relationship amount having a positive value is a reason (affirmative information) for affirming the inference result. A relationship amount having a negative value is a reason (negative information) for denying the inference result.

In step S705, the CPU 100 adds 1 to the variable j stored in the main memory 101.

In step S706, the CPU 100 compares the value of j with the combination count (mCk). If j is smaller than the combination count, since it is impossible to determine whether the relationship amounts associated with all $I_j$ satisfy the determination criterion, the process returns to step S703 to continue the processing. If j is larger than the combination count, the CPU 100 executes step S707.

In step S707, the CPU 100 displays, on the monitor 104, the posteriori probability of the inference $A_i$ obtained when $I_{fix}$ stored in the main memory 101 is input as evidences. This corresponds to the inference result desired by the user. In step S708, the CPU 100 adds 1 to the value of the variable i stored in the main memory 101. In step S709, the CPU 100 compares the value of i with the value of n. If i is smaller than n, since not all the inference results $A_i$ have been processed, the process returns to step S702 to continue the processing. If i is larger than n, the CPU 100 terminates the processing in step S205. With this processing, posteriori probabilities, affirmative information, and negative information are displayed for all the inference results $A_i$.

Cases in which k=1 and k=2 will be described below as concrete examples. Note that in comparative calculation, the differences between priori probabilities and posteriori probabilities are calculated. First of all, in step S601, the CPU 100 acquires 11.0%, 48.0%, and 41.0% as the priori probabilities of the inference results "abnormality type: primary lung cancer", "abnormality type: lung metastasis", and "abnormality type: other abnormalities", respectively.

FIG. 6 shows a case in which the medical information "size of nodus: intermediate" is selected from $I_{fix}$ input in step S503 by setting k=1, and is set as partial information $I_1$ of the fixed information. The CPU 100 performs inference by using $I_1$ as an evidence. The CPU 100 stores the resultant posteriori probabilities, 12.3%, 53.5%, and 34.2%, belonging to the inference results "abnormality type: primary lung cancer", "abnormality type: lung metastasis", and "abnormality type: other abnormalities" in association with $I_1$.

Table 3 shows all $I_j$ with k=1, the posteriori probabilities of the inference results $A_1$ to $A_n$ calculated by using $I_j$ as evidences, and differences $D(A_i|I_j)$ between the posteriori probabilities and the priori probabilities of the inference results $A_1$ to $A_n$. These differences are obtained by the processing in steps S603 to S605.

TABLE 3

| $I_j$ (k = 1) | $P(A_1|I_j)$ | $P(A_2|I_j)$ | $P(A_3|I_j)$ | $D(A_1|I_j)$ | $D(A_2|I_j)$ | $D(A_3|I_j)$ |
|---|---|---|---|---|---|---|
| Size of Nodus: Intermediate | 12.3% | 53.5% | 34.3% | 1.3% | 5.5% | −6.7% |
| Shape: Sphere | 4.5% | 65.9% | 29.6% | −6.5% | 17.9% | −11.4% |
| Soft Tissue Density Ratio: Low | 21.9% | 40.4% | 37.7% | 10.9% | −7.6% | −3.3% |
| Gas Density Ratio: High | 27.5% | 37.0% | 35.5% | 16.5% | −11.0% | −5.5% |
| Boundary: Unclear | 6.0% | 59.9% | 34.1% | −5.0% | 11.9% | −.6.9% |

$A_1$ Abnormality Type: Primary Lung Cancer   $P(A_1) = 11.0\%$
$A_2$ Abnormality Type: Lung Metastasis   $P(A_2) = 48.0\%$
$A_3$ Abnormality Type: Other Abnormalities   $P(A_3) = 41.0\%$ Table 4 shows an example of a method of calculating relationship amounts $C(A_i, I_j)$. In this case, relationship amounts are absolutely obtained in accordance with the differences between posteriori probabilities and priori probabilities. Table 5 shows the relationship amounts obtained by the calculation method indicated by table 4. These amounts are obtained by the processing in step S607.

TABLE 4

| $D(A_x|I_j)$ | $C(A_x, I_j)$ |
|---|---|
| 14.0%- | +4 |
| 10.0%-14.0% | +3 |
| 6.0%-10.0% | +2 |
| 2.0%-6.0% | +1 |
| −2./0%-2.0% | 0 |
| −6.0%--2.0% | −1 |
| −10.0%--6.0% | −2 |
| −14.0%--10.00 | −3 |
| --14.00 | −4 |

TABLE 5

| $I_j$ (k = 1) | $C(A_1, I_j)$ | $C(A_2, I_j)$ | $C(A_3, I_j)$ |
|---|---|---|---|
| Size of Nodus: Intermediate | 0 | +1 | −2 |
| Shape: Sphere | −2 | +4 | −3 |

TABLE 5-continued

| $I_j$ (k = 1) | $C(A_1, I_j)$ | $C(A_2, I_j)$ | $C(A_3, I_j)$ |
|---|---|---|---|
| Soft Tissue Density Ratio: Low | +3 | −2 | −1 |
| Gas Density Ratio: High | +4 | −3 | −1 |
| Boundary: Unclear | −1 | +3 | −2 |

Figure 12:
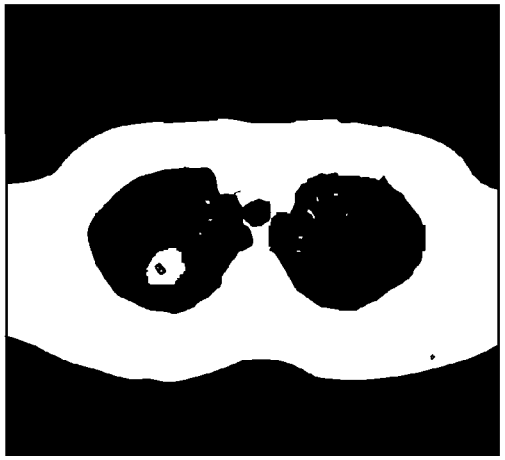
FIG. 12 is a view showing an example of display on a monitor 104 when k=1 in the second embodiment.

$A_1$ Abnormality Type: Primary Lung Cancer
$A_2$ Abnormality Type: Lung Metastasis
$A_3$ Abnormality Type: Other Abnormalities FIG. 12 shows an example of display on the monitor 104 when k=1 and the predetermined criterion in step S703 is set to the absolute value of a relationship amount which is 3 or more (in other words, relationship amounts of +4, +3, −3, and −4). In the above case, when i=1 and j=1 (size of nodus: intermediate), since the relationship amount is 0, it does not satisfy the criterion. The CPU 100 therefore skips the processing in step S704, and performs the processing in step S705. That is, the monitor 104 displays no data. In contrast, when i=1 (primary lung cancer) and j=4 (gas density ratio: high), since the relationship amount is +4, the amount satisfies the criterion. The CPU 100 therefore performs the processing in step S704.

In the above case, when the relationship amount is positive, it indicates that the posteriori probability of the inference result $A_i$ obtained when $I_j$ is input as an evidence becomes higher than the priori probability. When the relationship amount is negative, the corresponding information indicates that the posteriori probability becomes lower than the priori probability. Therefore, when the relationship amount is positive, the corresponding information becomes a reason for affirming the inference result $A_i$ whereas when the relationship amount is negative, the corresponding information becomes a reason for denying the inference result. When i=1 and j=4, therefore, "gas density ratio: high" is displayed as a reason for affirming the inference result $A_1$ (primary lung cancer) on the monitor 104.

When all the processing is complete, as shown in FIG. 12, the CPU 100 displays "abnormality type: primary lung cancer", "abnormality type: lung metastasis", and "abnormality type: other abnormalities" as the inference results $A_1$ to $A_n$, and 15.3%, 66.4%, and 18.3% as their posteriori probabilities.

The CPU 100 displays "soft tissue density ratio: low" and "gas density ratio: high" as reasons for affirming "abnormality type: primary lung cancer". In addition, the CPU 100 displays "shape: sphere" and "boundary: unclear" as reasons for affirming "abnormality type: lung metastasis", and "gas denying ratio: high" as a reason for denying "abnormality type: lung metastasis". Furthermore, the CPU 100 displays "shape: sphere" as a reason for denying "abnormality type: other abnormalities".

A case in which k=2 will be described next. In the following case, the relationship amount calculation processing in step S607 is performed by "a method of calculating the absolute values of the differences between calculated posteriori probabilities and priori probabilities for the respective partial sets, and normalizing the values with reference to the maximum value among them". As described in the first embodiment, FIG. 8 shows a case in which the pieces of medical information "size of nodus: intermediate" and "shape: sphere" are selected from $I_{fix}$ by setting k=2, and are set as partial information $I_1$ of the fixed information. The CPU 100 performs inference by using $I_1$ as an evidence and stores the resultant posteriori probabilities, 4.9%, 71.1%, and 24.0%, belonging to the inference results "abnormality type: primary lung cancer", "abnormality type: lung metastasis", and "abnormality type: other abnormalities" in association with $I_1$.

Table 6 shows all $I_j$ with k=2, the posteriori probabilities of the inference results $A_1$ to $A_n$, and the differences between the posteriori probabilities and the priori probabilities of the inference results $A_1$ to $A_n$. They are obtained by the processing in steps S603 to S605.

TABLE 6

| $I_j$ (k = 2) | | $P(A_1|I_j)$ | $P(A_2|I_j)$ | $P(A_3|I_j)$ | $D(A_1|I_j)$ | $D(A_2|I_j)$ | $D(A_3|I_j)$ |
|---|---|---|---|---|---|---|---|
| Size of Nodus: Intermediate | Shape: Sphere | 4.9% | 71.1% | 24.0% | −6.1% | 23.1% | −17.0% |
| Size of Nodus: Intermediate | Soft Tissue Density Ratio: Low | 24.2% | 44.6% | 31.2% | 13.2% | −3.4% | −9.8% |
| Size of Nodus: Intermediate | Gas Density Ratio: High | 30.2% | 40.6% | 29.2% | 19.2% | −7.4% | −11.8% |
| Size of Nodus: Intermediate | Boundary: Unclear | 6.6% | 65.4% | 28.0% | −4.4% | 17.4% | −13.0% |
| Shape: Sphere | Soft Tissue Density Ratio: Low | 9.8% | 60.5% | 29.7% | −1.2% | 12.5% | −11.3% |
| Shape: Sphere | Gas Density Ratio: High | 12.9% | 57.9% | 29.3% | 1.9% | 9.9% | −11.7% |
| Shape: Sphere | Boundary: Unclear | 2.3% | 75.2% | 22.5% | −8.7% | 27.2% | −18.5% |
| Soft tissue Density Ratio: Low | Gas Density Ratio: High | 46.2% | 26.3% | 27.5% | 35.2% | −21.7% | −13.5% |
| Soft tissue Density Ratio: Low | Boundary: Unclear | 12.8% | 53.8% | 33.4% | 1.8% | 5.8% | −7.6% |
| Gas Density Ratio: High | Boundary: Unclear | 16.7% | 50.8% | 32.5% | 5.7% | 2.8% | −8.5% |

$A_1$ Abnormality Type: Primary Lung Cancer  $P(A_1) = 11.0\%$
$A_2$ Abnormality Type: Lung Metastasis  $P(A_2) = 48.0\%$
$A_3$ Abnormality Type: Other Abnormalities  $P(A_3) = 41.0\%$ The CPU 100 obtains relationship amounts by the processing in step S607. In this case, the CPU 100 calculates the absolute values of $D(A_i|I_j)$ (to be referred to as difference amounts hereinafter) and normalizes them based on the maximum value among them. These amounts will be described specifically below. The maximum value of the absolute values of the difference amounts of "abnormality type: primary lung cancer" is 35.2%. The respective difference amounts are converted to convert this value into 4.0. If, for example, the difference amount is −4.4%, the relationship amount becomes −0.5. Thereafter, this value is rounded down to the nearest 1, and the obtained value is used as a relationship amount. That is, 4.0 is rounded down to +4, and −0.5 is rounded down to 0. This operation is also performed for "abnormality type: lung metastasis" and "abnormality type: other abnormalities". At this time, the value on which normalization is based changes in accordance with inference results. In this case, normalization is performed based on 27.2% in the case of "abnormality type: lung metastasis" and 18.5% in the case of "abnormality type: other abnormalities". Table 7 shows the relationship amounts obtained by the above method.

TABLE 7

| $I_j$ (k = 2) | | C ($A_1|I_j$) | C ($A_2|I_j$) | C ($A_3|I_j$) |
|---|---|---|---|---|
| Size of Nodus: Intermediate | Shape: Sphere | 0 | +3 | −3 |
| Size of Nodus: Intermediate | Soft Tissue Density Ratio: Low | +1 | 0 | −2 |
| Size of Nodus: Intermediate | Gas Density Ratio: High | +2 | −1 | −2 |
| Size of Nodus: Intermediate | Boundary: Unclear | 0 | +2 | −2 |
| Shape: Sphere | Soft Tissue Density Ratio: Low | 0 | +1 | −2 |
| Shape: Sphere | Gas Density Ratio: High | 0 | +1 | −2 |
| Shape: Sphere | Boundary: Unclear | 0 | +4 | −4 |
| Soft tissue Density Ratio: Low | Gas Density Ratio: High | +4 | −3 | −2 |
| Soft tissue Density Ratio: Low | Boundary: Unclear | 0 | 0 | −1 |
| Gas Density Ratio: High | Boundary: Unclear | 0 | 0 | −1 |

Figure 13:
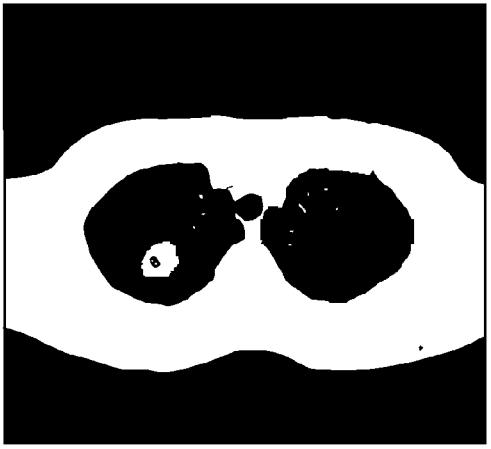
FIG. 13 is a view showing an example of display on the monitor 104 when k=2 in the second embodiment.

$A_1$ Abnormality Type: Primary Lung Cancer
$A_2$ Abnormality Type: Lung Metastasis
$A_3$ Abnormality Type: Other Abnormalities FIG. 13 shows an example of display on the monitor 104 when k=2 and the predetermined criterion in step S703 is set to the absolute value of a relationship amount which is 3 or more (in other words, relationship amounts of +4, +3, −3, and −4). As in the case of k=1, when the relationship amount is positive, the corresponding information becomes a reason for affirming the inference result $A_i$, whereas when the relationship amount is negative, the corresponding information becomes a reason for denying the inference result. As shown in FIG. 13, when all the processing is complete, the CPU 100 displays "abnormality type: primary lung cancer", "abnormality type: lung metastasis", and "abnormality type: other abnormalities" as the inference results $A_1$ to $A_n$ and 15.3%, 66.4%, and 18.3% as their posteriori probabilities.

The CPU 100 displays "soft tissue density ratio: low and gas density ratio: high" as reasons for affirming "abnormality type: primary lung cancer". In addition, the CPU 100 displays "size of nodus: intermediate and shape: sphere" and "shape: sphere, boundary: unclear" as reasons for affirming "abnormality type: lung metastasis", and "soft tissue density ratio: low and gas denying ratio: high" as reasons for denying "abnormality type: lung metastasis". Furthermore, the CPU 100 displays "size of nodus: intermediate and shape: sphere" and "shape: sphere and boundary: unclear" as reasons for denying "abnormality type: other abnormalities".

In either of the cases of k=1 and k=2, it is preferable to display the inference results $A_1$ to $A_n$ in descending order of posteriori probability calculated by using $I_{fix}$ as evidences, as shown in FIGS. 12 and 13. However, the present invention is not limited to this.

Displaying both reasons for affirming an inference result and reasons for denying the inference result can make the user consider the possibility of other inference results as well as determining the reliability of an inference result with the highest probability. In addition, as in the first embodiment, this can also prompt the user to verify the reliability of input medical information.

According to the arrangement described above, the following effects can be obtained:

(1) Presenting a reason for affirming each of a plurality of inference results and a reason for denying it makes it possible to not only determine the reliability of an inference result with the highest probability but also consider the possibility of other inference results.

(2) The arrangement can prompt the user to verify the reliability of input medical information.

Modification of Second Embodiment

When selecting partial information $I_j$ of fixed information in step S603, it is possible to select k pieces of information or less (for example, partial information with both k=1 and k=2) of $I_{fix}$. As a comparative calculation method in step S605, the method of calculating the difference values between probabilities has been exemplified. However, the present invention is not limited to this. For example, a method of calculating probability ratios may be used as a comparative calculation method in step S605. Other methods may also be used. In addition, it is possible to use a relationship amount calculation method in step S607 other than that described above. For example, relationship amounts may be calculated by a method of calculating logarithms. When a method like that described in the case of k=1 is to be used, the conversion width to be set is not limited to that shown in table 4. In the case of k=2, it is possible to use the round-up method, the round-off method, or other methods in place of the round-down method. Although the above case uses nine discrete values, the number of discrete values to be used is not limited to this. Furthermore, a relationship amount may take a continuous value.

The determination criterion to be used in step S703 is not limited to the method described above. The user may arbitrarily change the determination criterion. In this case, this apparatus preferably includes a user interface for the change of the determination criterion. In step S704, all the pieces of information $I_j$ satisfying the criterion are displayed. However, of all the pieces of information satisfying the criterion, only results which affirm/deny the inference result most may be displayed. Furthermore, if there is no reason for denying an inference result, a warning may be displayed. A determination criterion for this display of a warning may differ from that in step S703. It is, however, not desirable to perform determination based on a criterion milder than the determination criterion in step S703. When a relationship amount and $I_j$ are input as evidences, it is also possible to simultaneously display posteriori probabilities.

In step S707, all the inference results $A_1$ to $A_n$ are displayed. However, only an inference result with the highest posteriori probability may be displayed. Alternatively, only some inference results may be displayed. In this case, the user may determine the number of inference results to be displayed. In addition, inference results with posteriori probabilities exceeding a threshold, for example, posteriori probabilities equal to or more than 30%, may be displayed. However, the threshold to be set is not limited to the above example, and the user may determine a threshold.

Obviously, the modification described in the first embodiment in association with steps S201 and S204 can be applied to the second embodiment.

Third Embodiment

Figure 14:
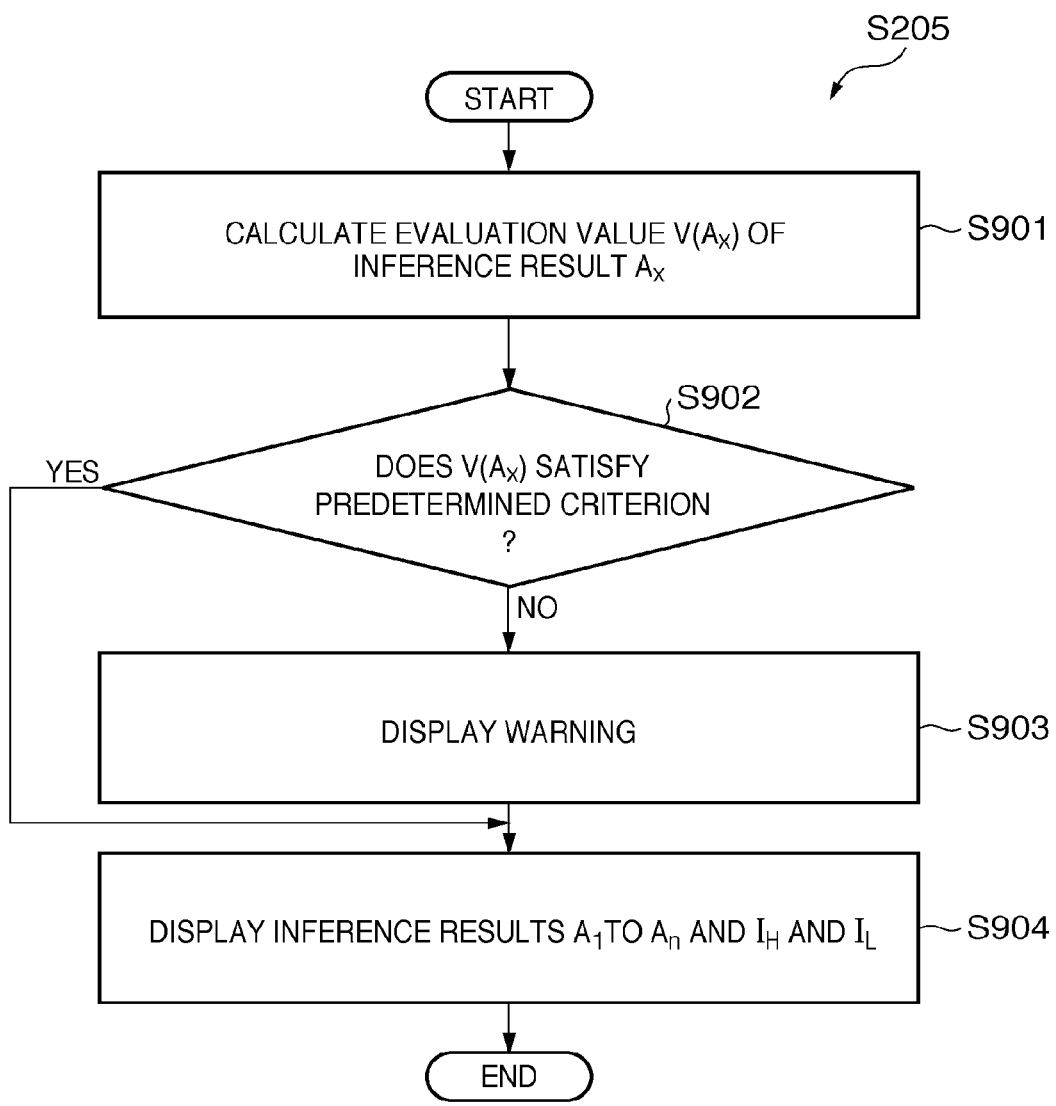
FIG. 14 is a flowchart showing a detailed processing procedure in step S205 in FIG. 2.

The third embodiment will be described next. Note that the arrangement of the third embodiment is the same as that of the first embodiment. For this reason, the block diagram of FIG. 1 will be used, and a description of the arrangement will be omitted. Control performed by a control unit 10 in the third embodiment is almost the same as that in the first embodiment (FIG. 2). FIG. 14 is a flowchart for explaining a procedure for inference result display processing (S205) in the third embodiment. Note that the processing shown in the flowchart of FIG. 14 is implemented by causing a CPU 100 to execute programs stored in a main memory 101. In step S205, the CPU 100 displays the results of inference processing performed in step S204. A detailed processing procedure in step S205 will be described in detail below with reference to FIGS. 14 and 15.

FIG. 14 is a flowchart showing a detailed processing procedure in step S205. In step S901, the CPU 100 calculates an evaluation value $V(A_x)$ of $A_x$ with the highest posteriori probability among the posteriori probabilities of $A_1$ to $A_n$ stored in the main memory 101. Note that this calculation method will be described later.

In step S902, the CPU 100 determines whether the evaluation value calculated in step S901 satisfies a predetermined criterion. If NO in step S902, the CPU 100 performs the processing in step S903. If YES in step S902, the CPU 100 skips the processing in step S903. In step S903, the CPU 100 displays a warning on the monitor 104. In step S904, the CPU 100 displays the result of inference processing performed in step S804. The CPU 100 displays the inference results $A_1$ to $A_n$, their posteriori probabilities, and $I_H$ and $I_L$ stored in the main memory 101 on the monitor 104. A concrete example of this operation will be described below.

Table 8 shows $I_{fix}$ input to the probability reasoning model in FIG. 4B in step S803, the posteriori probabilities of the inference results $A_1$ to $A_n$ (n=3), calculated by using $I_{fix}$ as evidences, and $I_H$ and $I_L$ when k=1.

TABLE 8

| $I_{fix}$ | Size of Nodus: Intermediate |
| | Smoothness: Intermediate |
| | Vascular Involvement/Involution: Unknown |
| | Soft Tissue Density Ratio: High |
| | Gas Density Ratio: Low |

TABLE 8-continued

| $A_1$ Abnormality Type: Primary Lung Cancer | 9.6% |
| $A_2$ Abnormality Type: Lung Metastasis | 49.9% |
| $A_3$ Abnormality Type: Other Abnormalities | 40.5% |
| $I_H$ | Vascular Involvement/Involution: Unknown |
| $I_L$ | Gas Density Ratio: Low |

In step S901, the CPU 100 calculates the evaluation value of a diagnosis result (abnormality type) having the highest posteriori probability among $A_1$ to $A_n$. In this case, the CPU 100 calculates an evaluation value $V(A_2)$ of $A_2$.

As a method of calculating the evaluation value $V(A_x)$ of $A_x$, there is available a method of calculating the difference between the probability of an inference result ($A_x$) with the highest posteriori probability and the probability of an inference result ($A_{x2}$) with the second highest posteriori probability. There is also available a method of calculating an evaluation value by using the probability of an inference result with the highest posteriori probability and the number of states (=n) of the inference result. These methods are expressed by equations (2) and (3), respectively.

[Mathematical 2]
$$V(A_x) = P(A_x \mid I_{fix}) - P(A_{x2} \mid I_{fix}) \quad (2)$$

[Mathematical 3]
$$V(A_x) = P(A_x \mid I_{fix}) - \frac{1}{n} \quad (3)$$

In this case, $P(A_x \mid I_{fix})$ indicates the posteriori probability of the inference result $A_x$ calculated by using $I_{fix}$ as evidences. In the case of table 8, the inference result $A_2$ exhibits the highest posteriori probability, and the inference result $A_3$ exhibits the second highest posteriori probability, which are 49.9% and 40.5%, respectively. In addition, n is 3, and its reciprocal is 1/n=0.333, which is 33.3% on a percentage basis. Calculating $V(A_2)$ by using equation (2) will produce $V(A_2)$=49.9%−40.5%=9.4%. Calculating $V(A_2)$ by using equation (3) will produce $V(A_2)$=49.9%−33.3%=16.6%.

In step S902, the CPU 100 determines whether $V(A_2)$ satisfies a predetermined criterion. In this case, the CPU 100 uses a threshold as the predetermined criterion, and performs determination depending on $V(A_2)$ is equal to or less than the threshold. If $V(A_2)$ is equal to or less than the threshold, the CPU 100 performs the processing in step S903. If $V(A_2)$ exceeds the threshold, the CPU 100 performs the processing in step S904. It is preferable that the user can change this threshold. In the case of table 8, when, for example, the threshold is 15%, the CPU 100 performs the processing in step S903 with respect to the evaluation value calculated by equation (2). In contrast, with the evaluation value calculated by equation (3), the CPU 100 skips the processing in step S903. In step S903, the CPU 100 displays a warning. In step S904, the CPU 100 displays $I_{fix}$, the posteriori probabilities of the inference results $A_1$ to $A_3$, and $I_H$ and $I_L$. FIG. 15 shows an example of display when a warning is displayed. In this case, a warning is displayed by using an icon calling attention and characters.

According to the above arrangement, the following effect can be obtained.

(1) Displaying a warning when an evaluation value calculated for an inference result satisfies a predetermined criterion can prompt the user to verify the reliability of the inference result and the reliability of input medical information.

Modification of Third Embodiment

It is also possible to calculate an evaluation value in step S901 by using a combination of equations (2) and (3). Equations other than equations (2) and (3) may also be used. The user may arbitrarily set a criterion in step S902. In this case, this apparatus preferably includes a user interface for setting conditions. However, the present invention is not limited to this. The criterion to be used is not limited to a threshold.

When displaying a warning in step S903, it is possible to display only an icon or characters. Alternatively, it is possible to use other methods as long as they take forms of calling attention to the user. For example, there is available a method of changing the display colors of characters, producing a warning sound, or changing a background color. In step S904, all the inference results $A_1$ to $A_n$ are displayed. It is, however, possible to display only an inference result with the highest posteriori probability. Alternatively, only some inference results may be displayed. In this case, the user may determine the number of inference results to be displayed. In addition, inference results with posteriori probabilities exceeding a threshold, for example, posteriori probabilities equal to or more than 30%, may be displayed. However, the threshold to be set is not limited to the above example, and the user may determine a threshold.

As has been described in detail above, according to the first to third embodiments, of a plurality of reasons for inference, reasons having great influences on an inference result are presented to the user. Presenting also reasons for denying the inference result can make the user feel the necessity to consider the reliability of medical information and inference results and diagnosis other than a presented inference result (an inference result exhibiting the highest probability). That is, there is provided a mechanism of examining the reliability of information input at the time of interpretation and the possibility of diagnosis other than that presented by the system.

Other Embodiments

Although embodiments have been described in detail above, the present invention can take embodiments as a system, apparatus, method, program, storage medium, and the like. More specifically, the present invention can be applied to a system including a plurality of devices, or to an apparatus including a single device.

The present invention is also implemented by executing the following processing. That is, the processing is executed by supplying software (programs) for implementing the functions of the above embodiments to the system or apparatus via a network or various types of storage media, and causing the computer (or the CPU or MPU) of the system or apparatus to read out and execute the programs.

The present invention is not limited to the above embodiments and various changes and modifications can be made within the spirit and scope of the present invention. Therefore, to apprise the public of the scope of the present invention, the following claims are made.

This application claims the benefit of Japanese Patent Application No. 2009-047021, filed Feb. 27, 2009 which is hereby incorporated by reference herein in its entirety.

The invention claimed is:

1. A diagnosis support apparatus comprising:
an inference unit configured to, based on a plurality of pieces of medical information, calculate an inference probability with respect to plural candidates of diagnosis name concerning medical diagnosis;
a calculation unit configured to calculate, for a plurality of partial sets, each including, as an element, at least one piece of medical information retrieved from the plurality of pieces of medical information, a degree of effect on a respective inference probability of at least one of the plural candidates of diagnosis name, the calculation unit being configured to calculate the degree of effect individually for the at least one of the plural candidates of diagnosis name; and
a display control unit configured to cause a display unit to display, as an inference result, the at least one of the plural candidates of diagnosis name, wherein the at least one of the plural candidates is specified based on the inference probability calculated by the inference unit, and to cause the display unit to display medical information included in a partial set of information retrieved from the plurality of pieces of medical information, wherein the partial set including the displayed medical information is retrieved from the plurality of pieces of medical information, based on the degree of effect calculated by the calculation unit based on the inference result.

2. The diagnosis support apparatus according to claim 1, wherein the calculation unit calculates a degree of denial or a degree of affirmation with respect to the inference result as a degree of effect on an inference probability of the inference result, and
wherein the display control unit causes the display unit to display, as affirmation information, medical information included in a partial set of the plurality of partial sets, for which the degree of affirmation is calculated by the calculation unit, and to display, as denial information, medical information included in a partial set, of the plurality of partial sets, for which the degree of denial is calculated by the calculation unit.

3. The diagnosis support apparatus according to claim 2, wherein the display control unit causes the display unit to display medical information included in a partial set for which a highest degree of denial is calculated by the calculation unit and medical information included in a partial set for which a highest degree of affirmation is calculated, as the denial information and the affirmative information, respectively.

4. The diagnosis support apparatus according to claim 1, wherein the inference unit calculates, for each of the plural candidates of diagnosis name to which a priori probability are set, an inference probability of each of the plural candidates of diagnosis name by calculating a posteriori probability based on the plurality of pieces of medical information.

5. The diagnosis support apparatus according to claim 4, wherein the calculation unit calculates the degree of effect for an inference result exhibiting a highest posteriori probability.

6. The diagnosis support apparatus according to claim 4, wherein the calculation unit calculates the degree of effect for each of the plural candidates of diagnosis name, and wherein the display control unit causes the display unit to display medical information of a partial set for which the degree of effect satisfies a predetermined condition, as one of affirmation information and denial information, for each of a plurality of inference results corresponding to the plural candidates of diagnosis name.

7. The diagnosis support apparatus according to claim 4, wherein the calculation unit calculates the degree of effect for each candidate, of the plural candidates of diagnosis name, whose posteriori probability calculated by the inference unit exceeds a predetermined value.

8. The diagnosis support apparatus according to claim 4, wherein the calculation unit calculates a posteriori probability of each inference result based on the partial set, and calculates the degree of effect by using the priori probability and the posteriori probability.

9. The diagnosis support apparatus according to claim 4, further comprising an evaluation unit configured to calculate an evaluation value for a highest posteriori probability of a plurality of posteriori probabilities calculated in association with the plural candidates of diagnosis name, based on the plurality of posteriori probabilities,
wherein the display control unit causes the display unit to display a warning associated with reliability of an inference result when the evaluation value does not satisfy a predetermined condition.

10. The diagnosis support apparatus according to claim 9, wherein the evaluation unit sets, as the evaluation value, a difference between the highest posteriori probability of the plurality of posteriori probabilities and a second highest posteriori probability.

11. The diagnosis support apparatus according to claim 9, wherein the evaluation unit sets, as the evaluation value, a difference between the highest posteriori probability of the plurality of posteriori probabilities and a reciprocal of the number of the plurality of posteriori probabilities.

12. The diagnosis support apparatus according to claim 1, wherein the inference unit obtains at least one of the plural candidates of diagnosis name as an inference result based on inference probabilities calculated for the plural candidates of diagnosis name respectively.

13. The diagnosis support apparatus according to claim 1, further comprising a result specifying unit configured to specify at least one of the plural candidates of diagnosis name as an inference result based on the inference probability calculated by the inference unit,
wherein the display control unit causes the display unit to display the at least one of the plural candidates of diagnosis name, which is specified as an inference result by the result specifying unit.

14. The diagnosis support apparatus according to claim 13, further comprising a partial set specifying unit configured to specify at least one partial set from the plurality of partial sets based on the degree of effect calculated for the inference result by the calculation unit,
wherein the display control unit causes the display unit to display medical information included in the at least one partial set specified by the partial set specifying unit.

15. A diagnosis support apparatus comprising:
an inference unit configured to, based on a plurality of pieces of medical information, calculate an inference probability with respect to plural candidates of diagnosis name concerning medical diagnosis;
a calculation unit configured to calculate, for a plurality of partial sets, each including, as an element, at least one piece of medical information retrieved from the plurality of pieces of medical information, a degree of effect on an inference probability of one of the plural candidates of diagnosis name; and
a display control unit configured to cause a display unit to display, as an inference result, at least one of the plural candidates of diagnosis name, wherein the at least one of the plural candidates is specified based on the inference probability calculated by the inference unit, and to cause the display unit to display medical information included in a partial set of information retrieved from the plurality of pieces of medical information, wherein the partial set including the displayed medical information is retrieved from the plurality of pieces of medical information, based on the degree of effect calculated by the calculation unit based on the inference result.

16. The diagnosis support apparatus according to claim 15, wherein the calculation unit calculates a degree of denial or a degree of affirmation with respect to the inference result, as a degree of effect on an inference probability regarding the inference result, and
wherein the display control unit causes the display unit to display, as affirmation information, medical information included in a partial set of the plurality of partial sets, for which a degree of affirmation is calculated by the calculation unit, and to display, as denial information, medical information included in a partial set of the plurality of partial sets, for which a degree of denial is calculated by the calculation unit.

17. The diagnosis support apparatus according to claim 16, wherein the display control unit causes the display unit to display medical information included in a partial set for which a highest degree of denial is calculated by the calculation unit and medical information included in a partial set for which a highest degree of affirmation is calculated, as the denial information and the affirmative information, respectively.

18. The diagnosis support apparatus according to claim 15, wherein the inference unit calculates, for each of the plural candidates of diagnosis name to which a priori probability are set, an inference probability of each of the plural candidates of diagnosis name by calculating a posteriori probability based on the plurality of pieces of medical information.

19. The diagnosis support apparatus according to claim 18, wherein the calculation unit calculates the degree of effect for an inference result exhibiting a highest posteriori probability.

20. The diagnosis support apparatus according to claim 18, wherein the calculation unit calculates the degree of effect for each of the plural candidates of diagnosis name, and
wherein the display control unit causes the display unit to display medical information of a partial set for which the degree of effect satisfies a predetermined condition, as one of affirmation information and denial information, for each of a plurality of inference results corresponding to the plural candidates of diagnosis name.

21. The diagnosis support apparatus according to claim 18, wherein the calculation unit calculates the degree of effect for each candidate of the plural candidates of diagnosis name, whose posteriori probability calculated by the inference unit exceeds a predetermined value.

22. The diagnosis support apparatus according to claim 18, wherein the calculation unit calculates a posteriori probability of each inference result based on the partial set, and calculates the degree of effect by using the priori probability and the posteriori probability.

23. The diagnosis support apparatus according to claim 18, further comprising an evaluation unit configured to calculate an evaluation value for a highest posteriori probability of a plurality of posteriori probabilities calculated in association with the plural candidates of diagnosis name, based on the plurality of posteriori probabilities, wherein the display control unit causes the display unit to display a warning associated with reliability of an inference result when the evaluation value does not satisfy a predetermined condition.

24. The diagnosis support apparatus according to claim 23, wherein the evaluation unit sets, as the evaluation value, a difference between the highest posteriori probability of the plurality of posteriori probabilities and a second highest posteriori probability.

25. The diagnosis support apparatus according to claim 23, wherein the evaluation unit sets, as the evaluation value, a difference between the highest posteriori probability of the plurality of posteriori probabilities and a reciprocal of the number of the plurality of posteriori probabilities.

26. The diagnosis support apparatus according to claim 15, further comprising a result specifying unit configured to specify at least one of the plural candidates of diagnosis name as an inference result based on an inference probability calculated by the inference unit, wherein the display control unit causes the display unit to display the at least one of the plural candidates of diagnosis name, which is specified as an inference result by the result specifying unit.

27. The diagnosis support apparatus according to claim 15, further comprising a partial set specifying unit configured to specify at least one partial set from the plurality of partial sets based on the degree of effect calculated for the inference result by the calculation unit, wherein the display control unit causes the display unit to display medical information included in the at least one partial set specified by the partial set specifying unit.

28. A diagnosis support system comprising:

an inference unit configured to, based on a plurality of pieces of medical information, calculate an inference probability with respect to plural candidates of diagnosis name concerning medical diagnosis;

a calculation unit configured to calculate, for each of a plurality of partial sets, each including, as an element, at least one piece of medical information retrieved from the plurality of pieces of medical information, a degree of effect on a respective inference probability of the plural candidates of diagnosis name, the calculation unit being configured to calculate the degree of effect individually for each of the plural candidates of diagnosis name; and a display control unit configured to cause a display unit to display, as an inference result, at least one of the plural candidates of diagnosis name, wherein the at least one of the plural candidates is specified based on the inference probability calculated by the inference unit and to cause the display unit to display medical information included in a partial set of information retrieved from the plurality of pieces of medical information, wherein the partial set including the displayed medical information is retrieved from the plurality of pieces of medical information based on the degree of effect calculated by the calculation unit based on the inference result.

29. A diagnosis support system comprising:

an inference unit configured to, based on a plurality of pieces of medical information, calculate an inference probability with respect to plural candidates of diagnosis name concerning medical diagnosis;

a calculation unit configured to calculate, for each of a plurality of partial sets, each including, as an element, at least one piece of medical information retrieved from the plurality of pieces of medical information, a degree of effect on an inference probability of one of the plural candidates of diagnosis name; and a display control unit configured to cause a display unit to display, as an inference result, at least one of the plural candidates of diagnosis name, wherein the at least one of the plural candidates is specified based on the inference probability calculated by the inference unit, and to cause the display unit to display medical information included in a partial set of information retrieved from the plurality of pieces of medical information, wherein the partial set including the displayed medical information is retrieved from the plurality of pieces of medical information, based on the degree of effect calculated by the calculation unit based on the inference result.

30. An information processing method of diagnosis support, the method comprising:

calculating, based on a plurality of pieces of medical information, an inference probability with respect to plural candidates of diagnosis name concerning medical diagnosis;

calculating, for a plurality of partial sets each including, as an element, at least one piece of medical information retrieved from the plurality of pieces of medical information, a degree of effect on a respective inference probability of at least one of the plural candidates of diagnosis name, wherein the degree of effect is calculated individually for the at least one of the plural candidates of diagnosis name; and controlling a display unit to display, as an inference result, the at least one of the plural candidates of diagnosis name, wherein the at least one of the plural candidates is specified based on the calculated inference probability and to display medical information included in a partial set of information retrieved from the plurality of pieces of medical information, wherein the partial set including the displayed medical information is retrieved from the plurality of pieces of medical information, based on the degree of effect calculated based on the inference result.

31. An information processing method of diagnosis support, the method comprising:

calculating, based on a plurality of pieces of medical information, an inference probability with respect to plural candidates of diagnosis name concerning medical diagnosis;

calculating, for a plurality of partial sets each including, as an element, at least one piece of medical information retrieved from the plurality of pieces of medical information, a degree of effect on an inference probability of one of the plural candidates of diagnosis name; and controlling a display unit to display, as an inference result, at least one of the plural candidates of diagnosis name, wherein the at least one of the plural candidates is specified based on the calculated inference probability and to display medical information included in a partial set of information retrieved from the plurality of pieces of medical information, wherein the partial set including the displayed medical information is retrieved from the plurality of pieces of medical information, based on the degree of effect calculated based on the inference result.

32. A non-transitory computer readable storage medium storing a computer program for causing a computer to perform an information processing method of diagnosis support, the method comprising:
   calculating, based on a plurality of pieces of medical information, an inference probability with respect to plural candidates of diagnosis name concerning medical diagnosis;
   calculating, for a plurality of partial sets each including, as an element, at least one piece of medical information retrieved from the plurality of pieces of medical information, a degree of effect on a respective inference probability of at least one of the plural candidates of diagnosis name,
   wherein the degree of effect is calculated individually for the at least one of the plural candidates of diagnosis name; and
   controlling a display unit to display, as an inference result, the at least one of the plural candidates of diagnosis name, wherein the at least one of the plural candidates is specified based on the calculated inference probability and to display medical information included in a partial set of information retrieved from the plurality of pieces of medical information, wherein the partial set including the displayed medical information is retrieved from the plurality of pieces of medical information, based on the degree of effect calculated based on the inference result.

33. A non-transitory computer readable storage medium storing a computer program for causing a computer to perform an information processing method of diagnosis support, the method comprising:
   calculating, based on a plurality of pieces of medical information, an inference probability with respect to plural candidates of diagnosis name concerning medical diagnosis;
   calculating, for a plurality of partial sets each including, as an element, at least one piece of medical information retrieved from the plurality of pieces of medical information, a degree of effect on an inference probability of one of the plural candidates of diagnosis name; and
   controlling a display unit to display, as an inference result, at least one of the plural candidates of diagnosis name, wherein the at least one of the plural candidates is specified based on the calculated inference probability and to display medical information included in a partial set of information retrieved from the plurality of pieces of medical information, wherein the partial set including the displayed medical information is retrieved from the plurality of pieces of medical information, based on the degree of effect calculated based on the inference result.

* * * * *